United States Patent [19]

Sugai et al.

[11] Patent Number: 5,976,742
[45] Date of Patent: Nov. 2, 1999

[54] NAPHTHOQUINONE DERIVATIVE AND ELECTROPHOTOGRAPHIC MATERIAL USING THE NAPHTHOQUINONE DERIVATIVE

[75] Inventors: Fumio Sugai; Nobuko Akiba; Kazunari Hamasaki, all of Osaka, Japan

[73] Assignee: Mita Industrial Co., Ltd., Osaka, Japan

[21] Appl. No.: 09/083,981

[22] Filed: May 26, 1998

[30] Foreign Application Priority Data

May 23, 1997 [JP] Japan ................................. 9-133596

[51] Int. Cl.[6] ................................................. G03G 5/04
[52] U.S. Cl. ........................... 430/56; 430/58.25; 430/83
[58] Field of Search ............................. 544/344; 430/83, 430/56, 78, 58.25

[56] References Cited

U.S. PATENT DOCUMENTS

| | | | |
|---|---|---|---|
| 4,960,886 | 10/1990 | Mukai et al. | 544/344 |
| 5,328,789 | 7/1994 | Nakamori et al. | 430/83 |
| 5,449,580 | 9/1995 | Nakamori et al. | 430/83 |
| 5,460,909 | 10/1995 | Shoshi et al. | 430/83 |
| 5,718,997 | 2/1998 | Hayata et al. | 430/83 |

OTHER PUBLICATIONS

Chemical Abstracts 68:38925, 1968.
Chemical Abstracts 67:3068, 1967.

*Primary Examiner*—Christopher D. Rodee
*Attorney, Agent, or Firm*—Sherman and Shalloway

[57] ABSTRACT

The present invention provides a novel naphthoquinone derivative preferred as an electron transporting agent and an electrophotographic photosensitive material of high sensitivity which contains a novel naphtoquinone derivative having a general formula (1)

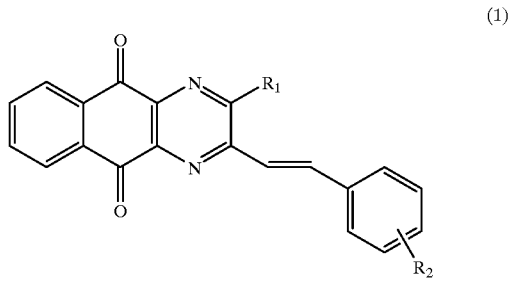

(1)

wherein $R^1$ represents a hydrogen atom, an alkyl group which may have a substituent, or an aryl group which may contain a substituent, and $R^2$ represents a hydrogen atom, an alkyl group which may have a substituent, a halogenated alkyl group, an aldehyde or a nitro group. The derivative is contained in a photosensitive layer of an electrophotographic photosensitive material as an electron transporting agent.

3 Claims, 13 Drawing Sheets

NAPHTHOQUINONE DERIVATIVE AND ELECTROPHOTOGRAPHIC MATERIAL USING THE NAPHTHOQUINONE DERIVATIVE

BACKGROUND OF THE INVENTION +ps
[TECHNICAL FIELD TO WHICH THE INVENTION BELONGS]

The present invention relates to a novel naphthoquinone derivative and to an electrophotographic material used in an image forming apparatus such as an electrostatic copying machine, a facsimile and a laser beam printer.

[PRIOR ART]

In image-forming apparatuses such as copying machines using the Carlson processing, a facsimile and a laser printer, electrophotographic materials using various materials have been used. The first of such electrophotographic materials is an inorganic photosensitive material in which an inorganic material such as selenium is used as a photosensitive layer, and the other is an organic photosensitive material using an organic material (OPC) as a photosensitive layer. The organic photosensitive material is cheaper than the inorganic photosensitive material and has higher productivity and is non-polluting. Hence, wide investigations have been carried out with regard to organic photosensitive materials.

Many organic photosensitive materials are so-called function-separating type photosensitive materials which are laminated-type photosensitive materials in which a charge generating layer and a charge transporting layer are laminated, but so-called single layer-type photosensitive materials obtained by dispersing a charge generating agent and a charge transporting agent in a single photosensitive layer are also known.

The charge transporting agent used in such a photosensitive material are required to have a high carrier movability. Since most of charge transporting agents having high carrier movability are positive hole transporting, the organic photosensitive materials are limited to negatively charged laminated-type organic photosensitive materials in which a charge transporting layer is provided at the outermost layer from the viewpoint of mechanical strength. However, because the negatively charged organic phososensitive material utilizes negatively polar corona dischage, the amount of ozone generated is large, and a problem of contaminating the environment or of deteriorating the photosensitive material occurs.

To remove such a problem, the use of an electron transporting agent as the charge transporting agent has been investigated, and for example, Japanese Laid-Open Patent Publication No. 206349/1989 proposes the use of a compound having a diphenoquinone structure or a benzoquinone structure as an electron transporting agent of an electrophotographic photosensitive material.

Japanese Laid-Open Patent Publication No. 110227/1994 proposes the use of a compound having a benzoquinone structure or a naphthoquinone structure as an electron trasporting agent for an electron photosensitive material.

However, conventional electron transporting agents such as generally diphenoquinone derivatives, benzoquinone derivatives, and naphthoquinone derivatives have been difficult to match with charge generating agents, and electron injection from charge generating agent to a charge transporting agent becomes insufficient. Such electron transporting agents have poor solubility in binder resins, the hopping distance becomes long, and movabillity of electrons in a low electric field is difficult to occur. Therefore, photosensitive materials containing conventional electron transporting agents, as is clear from the photosensitivity tests described in Examples, the residual potential becomes high, and the sensitivity is low.

As stated above, many of organic photosensitive materials now put to practical use contain a laminated-type photosensitive layer, but in comparison with the above type, photosensitive materials equipped with a single layer phosensitive layer has a simple structure and is easy to produce. In addition, it has many advantages, for example, it suppresses the occurrence of the film defects, and optical characteristics will be increased.

In addition, a photosensitive material equipped with a photosensitive layer of a single layer type conjointly uses an electron transporting agent and a positive hole transporting agent as a charge transporting agent can be used as a positive charging type and a negative charging type and the applicability range of the. photosensitive material can be extended. However, the conventional electron transporting agent and the positive hole transporting agent by their interaction poses a problem of obstructing the transporting of an electron and a positive hole. Hence, a photosensitive material equipped with a single layer type photosensitive layer has not been widely put into practical utility.

[SUMMARY OF THE INVENTION]

The object of this invention is to solve the above-mentioned technical problem, and to provide a preferred novel compound useful as an electron transporting agent in an electrophotographic material, and an electrophotographic material having the above novel compound which electrophotographic material has a higher sensitivity than heretofore.

The naphthoquinone derivative of this invention for solving the above problem is expressed by general formula (1)

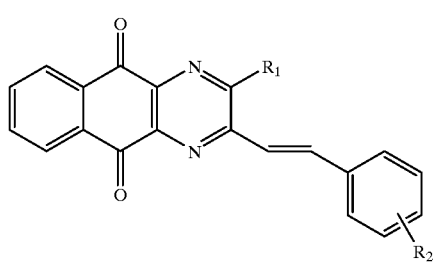

(1)

wherein $R_1$ represents a hydrogen atom, an alkyl group which may have a substituent, or an aryl group which may have a substituent, $R_2$ represents a hydrogen atom, an alkyl group which may have a substituent, a halogenated alkyl group, an aldehyde group, a nitro group, or a group (i):

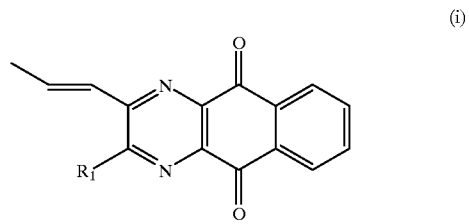

(i)

The naphthoquinone derivative of this invention expressed by the general formula (1) has excellent electron acceptability by the action of a group which the naphthoquinone ring has, namely by the action of $>C=O$, and by the action of the group $R_1$, the naphthoquinone derivative of this invention has a good solubility in a solvent, and a good mutual solubility in a binder resin. Because the above compound of formula (1) is uniformly dispersed in a photosensitive material, the hopping distance of an electron is short, especially it has excellent electron transportability in a low electric field, and matching with a charge generating agent is excellent. Accordingly, by using the derivative (1) as an electron transporting agent in an electronphotographic material, a highly sensitive electrosensitive material can be provided.

Since the naphthoquinone derivative (1) of this invention is obtained by bonding two naphthoquinone rings which inherently have excellent electron transportability and electron acceptability by the action of the above substituents, it is surmised that an increase in electron transportability can be seen.

The naphthoquinone derivative (1) of this invention can also be used as a solar battery and an EL element by utilizing its high electron transportability.

The electrophotographic material of this invention is composed of a conductive substrate and a photosensitive layer provided thereon. This photosensitive layer is characterized in that it contains a naphthoquinone derivative represented by the general formula (1) of this invention.

The photosensitive layer containing the naphthoquinone layer (1) mentioned above has excellent transportability in a low electric field and the proportion of re-bonding an electron to a positive hole in the layer decreases and when the apparent occurrence of charging efficiency approaches an actual value, the sensitivity of the photosensitive material increases. Furthermore, the residual potential of the photosensitive material becomes low, and the stability and durabililty also increase at the time of repeating exposure.

Especially since the naphthoquinone derivative (1) does not cause the interaction with positive hole transporting agent, which hamper the transportation of an electron and a positive hole, when it is used in the photosensitive layer of the single layer-type containing the positive hole transporting agent in the same layer, it is possible to prepare a photosensitve body having high sensitivity.

When the photosensitive material contains an electron transporting agent having an oxidation-reduction potential of −0.8 to −1.4 V, the sensitivity of the photosensitive material is further increases.

Since the electron transporting agent extracts an electron from a charge generating agent and trasmits it to the naphthoquinone derivative (1), it is surmised that injection of an electron from the charge generating agent to the naphthoquinone derivative (1) will become smoother.

In view of affinity for the naphthoquinone derivative (1), the electron transporting agent may preferably be a diphenoquinone derivative of general formula (2)

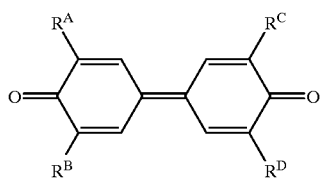

(2)

wherein $R^A$, $R^B$, $R^C$ and $R^D$ may be the same or different and each represents a hydrogen atom, an alkyl group, an alkoxy group, an aryl group, an aralkyl group, a cycloalkyl group, or an amino group, or preferably a benzoquinone derivative of the general formula (3)

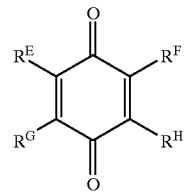

(3)

wherein $R^E$, $R^F$, $R^G$ and $R^H$ may be the same or different, and each represents a hydrogen atom, an alkyl group, an alkoxy group, an aryl group, an aralkyl group, a cyloalkyl group, or an amino group which may have a substituent.

BREIF DESCRIPTION OF THE DRAWINGS

DETAILED DESCRIPTION OF PREFERRED EMBODIMENTS OF THE INVENTION

Figure 1:
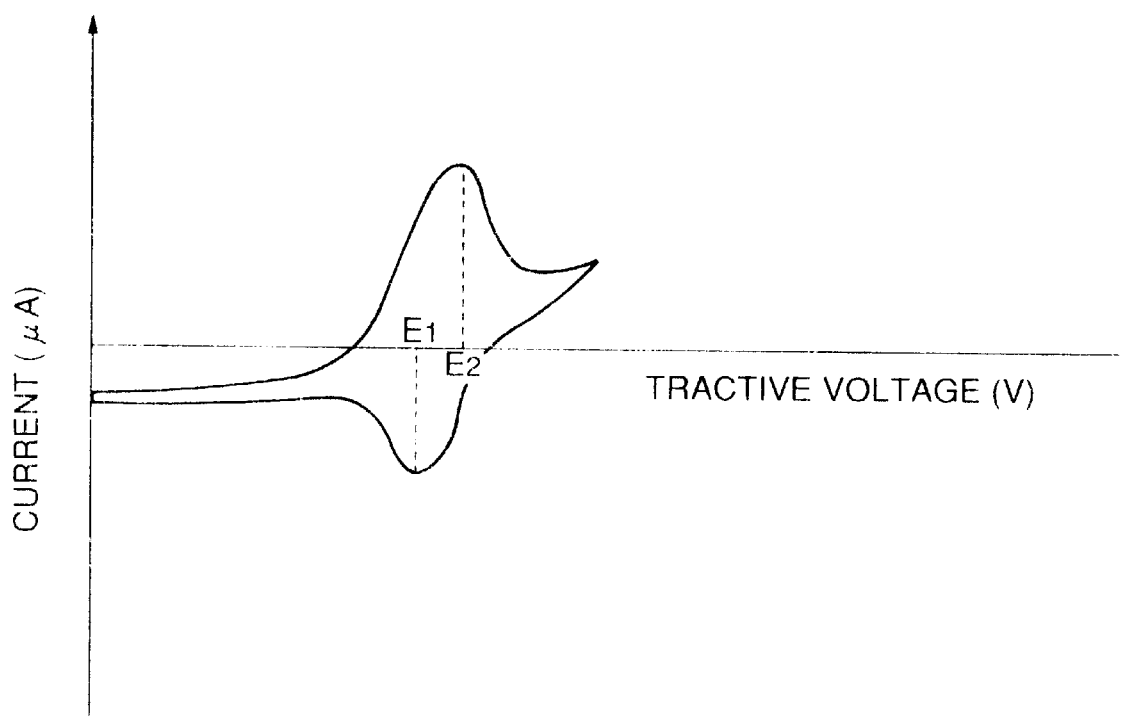
FIG. 1 shows a graph showing the relation between a traction voltage (V) and a current (A) for seeking oxidation reduction potential in this invention.

First of all, the naphthoquinone derivative (1) to be used in the electrophotographic photosensitive material of the invention will be described in details.

In the naphthoquinone derivative (1) expressed by the general formula (1), the alkyl group corresponding to the group $R_1$ include groups having 1 to 6 carbon atoms such as methyl, ethyl, n-propyl, isopropyl, n-butyl, isobutyl, s-butyl, t-butyl, pentyl and hexyl. The above alkyl groups may have a substituent. Examples of the substituent include an aralkyl group, an alkoxy group, an alkanoyl group, a halogen atom, an aryl group, or an alkoxycarbonyl group.

The aryl group corresponding to the group $R_1$ includes phenyl, tolyl, xylyl, bipheniryl ($C_6H_5C_6H_4$-), o-terphenyl, naphthyl, anthoryl and phenanthoryl. The above aryl groups may have a substitutent. Examples of the substituent include an alkyl group, an aralkyl group, an alkoxy group, an alkanoyl group, a halogen atom, or an alkoxycarbonyl group.

The alkyl groups may include the same alkyl groups as mentioned above.

Examples of the halogen atoms may include fluorine, chlorine, bromine, and iodine. Examples of the alkoxy group may include alkoxy groups having 1 to 6 carbon atoms such as methoxy, ethoxy, propoxy, isopropoxy, butoxy, isobutoxy, s-butoxy, t-butoxy, pentyloxy and hexyloxy.

Examples of the aralkyl groups include aralkyl groups having 1 to 6 carbon atoms in the alkyl portion, such as benzyl, 1-phenylethyl, 3-phenylpropyl, 4-phenylbutyl, 5-phenylpentyl and 6-phenylhexyl.

Examples of the alkoxycarbonyl groups include alkoxycarbonyl groups having 1 to 6 carbon atoms in the alkoxy portion, such as methoxycarbonyl, ethoxycarbonyl, propoxycarbonyl, isopropoxycarbonyl, butoxycarbonyl, t-butoxycaronyl, pentyloxycarbonyl, and hexyloxycarbonyl.

Examples of the alkanoyl groups include alkanoyl groups having 1 to 6 carbon atoms, such as acetyl, propionyl, butyryl, isobutyryl, pentanoyl, t-butylcarbonyl, and hexanoyl.

The alkyl groups corresponding to the group $R_2$ may be the same as cited in regard to the group $R_1$. The halogen and alkyl group in the halogenated alkyl groups corresponding to the group $R_2$ may be the same as the above.

Specific examples of the naphthoquinone derivative (1) represented by the general formula (1) include the following formulae (1-1) to (1-7).

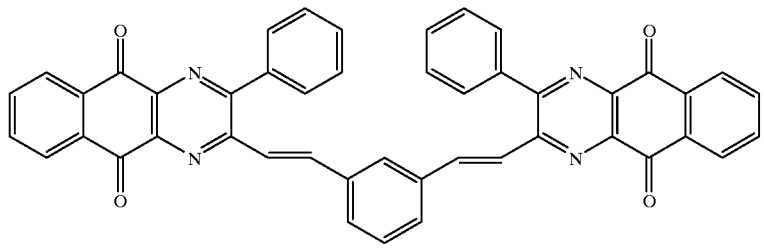
(1-1)

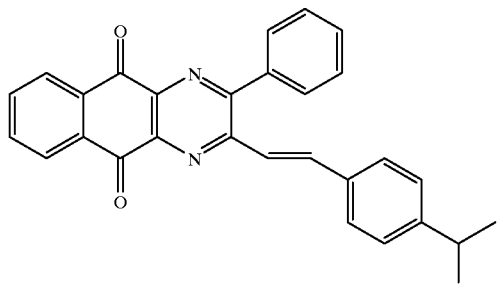
(1-2)

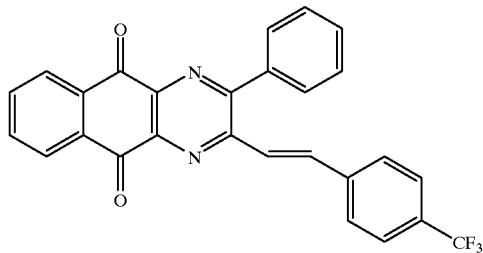
(1-3)

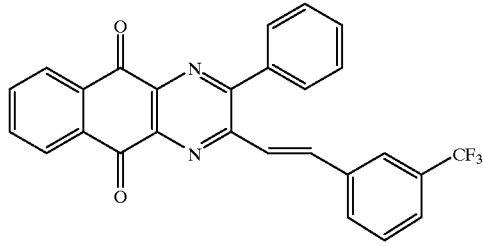
(1-4)

(1-5)

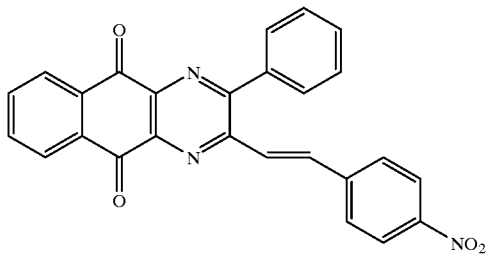

(1-6)

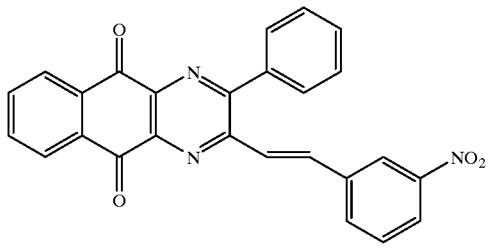

(1-7)

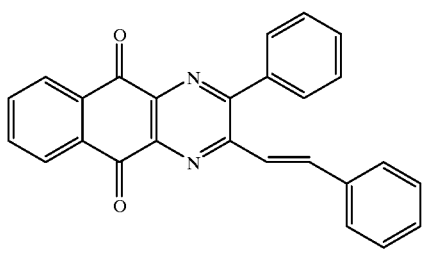

The naphthoquinone derivative represented by the general formula (1) is synthesized as shown in the following reaction formula.

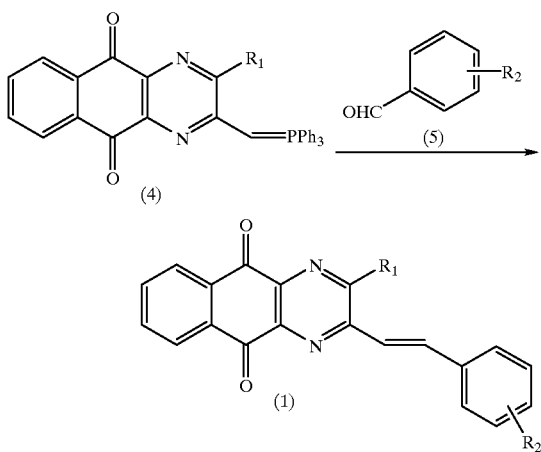

(wherein $R_1$ and $R_2$ are the same as above.)

This reaction of the naphthoquinone derivative of the general formula (4) is carried out with an aldehyde shown by the general formula (5) in a suitable solvent to obtain the naphthoquinone derivative (1).

The proportion of the aldehyde (5) to the compound (4) may preferably be 1:1 to 1:1.5 when the compound (1-2), (1-3), (1-4), or (1-5) is to be synthesized, and may preferably be 1:0.9 when the compound (1-1) is to be synthesized.

The reaction is usually carried out at 60 to 110° C., preferably 100 to 110° C., and is terminated after about 3 hours.

The electrophotographic photosensitive material of this invention will be described below in details.

The electrophotographic photosensitive material of this invention may be obtained by providing a photosensitive material containing a naphthoquinone derivative (1) expressed by the general formula (1) on an electroconductive substrate as mentioned above.

The electrophotographic photosensitive material of this invention may be a single layer type or a laminated type, but the effect obtained by the use of an electron transporting agent appears markedly in a single layer type photosensitive material.

The single layer-type electrophotographic photosensitive material is composed of a single photosensitive layer provided on an electroconductive substrate. This photosentive layer is composed of a binder resin containing a naphthoquinone derivative (1) as an electron transporting agent at least together with a charge generating agent and a positive hole transporting agent.

This single layer type electrophotographic photosensitive material can be applied to a positive charging and a negative charging, but preferably it is applied to a positive charging.

On the other hand, the laminated-type electrophotographic photosensitive material contains at least charge generating layer and an electron transporting layer provided in this sequence on an electroconductive substrate, and the charge transporting layer contains a naphthoquinone derivative (1) as an electron transporting agent. This laminated-type electrophotographic photosensitive material has a residual potential greatly decreased than the conventional laminated-type electrophotographic photosensitive material, and its sensitivity is increased. Since giving or receiving of an electron from a charge generating layer to an electron transporting layer or to a charge generating layer from an electron transporting layer is carried out smoothly, it is preferred to include a naphthoquinone derivative (1) in a charge generating layer.

Since the naphthoquinone derivative (1) used in the electrophotographic photosensitive material has a good solubility in a solvent and a good mutual solubility in a binder resin, and has excellent matching with the charge generating agent, the injection of an electron is carried out smoothly, and electron transportability in a low electric field is especially good.

Accordingly, for example, in a positive charging single type photosensitive material, an electron discharged from a charge generating agent in an exposing step is injected smoothly into an electron transporting agent composed of a naphthoquinone derivative (1) represented by the general formula (1). Then, by the donation and receiving of an electron between electron transporting agents, the electron moves to the surface of the photosensitive layer and a positive charge (+) charged positively on the surface of the photosensitive material in advance is cancelled. On the other hand, a positive hole (+) is injected into a positive hole transporting agent, and without being trapped on the way, the positive hole moves to the surface of the electroconductive substrate and cancels a negative charge (−) on the surface of the electroconductive substrate. In this way, the sensitivity of the positively charging single layer type photosensitive material is considered to increase. The negative charging single layer type photosensitive material becomes opposite in the direction of charge transfer from the above and the sensitivity increases in the same way.

Furthermore, in a positively chargeable laminated-type photosensitive material, an electron released from a charge generating agent in a charge generating layer in an exposing step is smoothly injected into an electron transporting agent composed of the naphthoquinone derivative expressed by the general formula (1) in the charge transporting layer. Then, by giving and receiving an electron between electron transporting agents, the electron transfers into the charge transporting layer, reaches the surface of the photosensitive layer, and cancels a positive charge (+) charged on the surface of the photosensitive layer in advance. On the other hand, the positive hole (+) moves from the charge generating layer directly to the surface of the electroconductive substrate, and cancels a negative charge (−) on the surface of the electroconductive substrate. In this way, the sensitivity of the positively chargeable laminated-type photosensitive material is considered to increase.

The charge generating agent which adsorbed light by exposure to the photosensitive material forms an ion pair [a positive hole (+) and an electrom (−). In order that the formed ion pair may become a free carrier and effectively cancel a surface charge, the proportion of the ion pair being re-bonded and vanished may preferably be small.

The electrophotographic photosensitive material of this invention can conjointly use the above-mentioned naphthoquinone derivative (1) and another electron transporting agent. Particularly, an electron transporting agent having an oxidation-reduction potential of −0.8 to −1.4 V is preferably used. The reason for this is as follows.

When an electron transporting agent having an oxidation-reduction potential of less than −1.4 V is used, the energy level of LUMO (this refers to an orbit having the lowest energy level among molecular orbits not having an electron. Usually, an excited electron moves in this orbit.) becomes higher than the charge generating agent. At the time of forming an ion pair, an electron does not move to an electron transporting agent, and this does not lead to an increase in the efficiency of occurrence of charge.

On the other hand, when an electron transporting agent having an oxidation-reduction potential of larger than −1.4 is used, since the energy level of LUMO is lower than the charge generating agent, an electron moves to the electron transporting agent at the time of producing an ion pair, and the ion pair is easy to separate to the carrier. That is to say, the electron transporting agent acts on the generation of a charge, and the efficiency of occurrence is increased.

On the other hand, in order to maintain a high sensitivity, it is necessary that during transfer of a free carrier, carrier trapping should not occur due to impurities.

Usually, in a moving step of a free carrier, a trap due to small amounts of impurities exists and the free carrier moves while repeating trapping—de-trapping. But when an electron transporting agent having an oxidation-reduction potential of larger than −0.8 V is used, the separared free carrier is dropped to a level at which de-trapping is impossible and the carrier trapping is formed, accordingly, the movement of the free carrier is stopped.

On the other hand, when an electron transporting agent having an oxidation-reduction potential of smaller than −0.8 V is used, no carrrier trap occurs, and the free carrier can easily move.

The above-mentioned oxidation-reduction potential, as shown in FIG. 1, was calculated from the following formula by seeking $E_1$ and $E_2$ shown in FIG. 1 from the relation between the traction voltage (V) and the current ($\mu$A).

Oxidation-reduction potential (V)=$(E_1+E_2)/2$

The traction voltage (V) and the current ($\mu$A) were measured by a 3-electrode type cyclic voltametry using a measuring solution prepared by compounding the following materials.

Electrodes: acting electrode (glassy carbon electrode), counter electrode (platinum electrode)

Reference electrode: silver nitrate electrode (0.1 mole/liter $AgNO_3$- acetonitrile solution)

Measuring solution Electrolyte: tetra-n-butyl ammonium perchlorate 0.1 mole

Measuring substance: 0.001 mole electron transporting agent

Solvent: $CH_2Cl_2$ 1 liter

The above materials were compounded to prepare a measuring solution.

Such an electron transporting agent is not limited if its oxidation-reduction potential is within the range of −0.8 to −1.4 V. Examples are benzoquinone type compounds; naphthoquinone-type compounds; anthraquinone-type compounds; diphenoquinone-type compounds; malonitrile-type compounds; thiopyran-type compounds; 2,4,8-trinitrothioxanethone; fluorenone-type compounds such as 3,4,5,7-tetranitro-9-fluorenone; dinitroanthracene; dinitroacridine;nitroanthraquinone; and dinitroanthraquinone.

When the compatibility with the charge generating agent or with the naphthoquinone derivative (1) of this invention is considered, those compounds belonging to the diphenoquinone-type compounds represented by the general formula (2) or belonging to the benzoquinone-type compounds represented by the general formula (3) and having an oxidation-reduction potential within the above-mentioned range are most preferably used.

The $R^A$, $R^B$, $R^C$ and $R^D$ in the above formula are not limited, but at least two of the above groups may preferably be the same groups.

In the above formula, the alkyl groups, the aralkyl groups, the alkoxy groups and aryl groups may be the same as described above.

Examples of the cycloalkyl groups may include cycloalkyl groups having 3 to 6 carbon atoms such as cyclopropyl, cyclobutyl, cyclopentyl and cyclohexyl groups.

As the amino group which may have a substituent, amino, monomethylamino, dimethylamino, monoethylamino, and diethylamino groups may be cited.

Specific examples of the diphenoquinone-type compounds are 3,5-dimethyl-3',5'-di(t-butyl)-4,4'-diphenoquinone (having an oxidation-reduction potential of −0.86 V) expressed by the formula (2-1) and 3,5,3',5'-tetrakis(t-butyl)-4,4'-diphenoquinone (having an oxidation-reduction potential of −0.94 V) expressed by the formula (2-2).

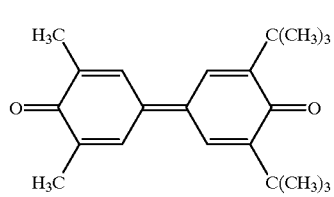
(2-1)

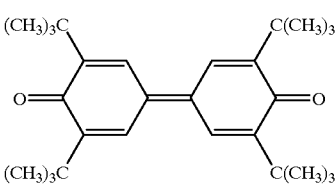
(2-2)

Specific examples of the benzoquinone-type compounds are p-benzoquinone (having an oxidation-reduction potential of −0.81 V) expressed by the formula (3-1) and 2,6-di(t-butyl)-p-benzoquinone (having an oxidation-reduction reduction potential of −1.31 V) expressed by the formula (3-2).

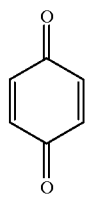
(3-1)

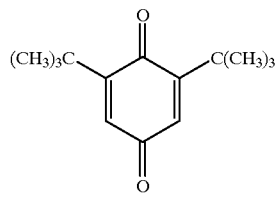
(3-2)

These electron transporting agents may be used singly or as a mixture of at least two compounds.

In the present invention, in addition to the above-mentioned electron transporting agent, another known conventional electron transporting agent may be included in the photosensitive layer. For example, such other electron transporting agent may be selected from compounds expressed by the general formula (ET1) to (ET16).

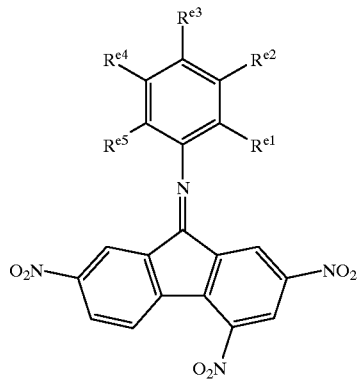
(ET1)

wherein $R^{e1}$, $R^{e2}$, $R^{e3}$, $R^{e4}$ and $R^{e5}$ may be the same or different and each represents a hydrogen atom, an alkyl group which may have a substituent, an alkoxy group which may have a substituent, an aryl group which may have a substituent, an aralkyl group which may have a substituent, a phenoxy group which may have a substituent, or a halogen atom.

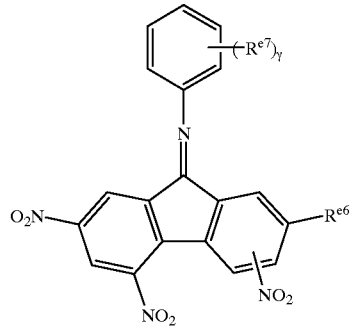
(ET2)

wherein $R^{e6}$ represents an alkyl group, and $R^{e7}$ represents an alkyl group which may have a substituent, an alkoxy group which may have a substituent, an aryl group which may have a substituent, an aralkyl group which may have a substituent, a halogen atom, or a halogenated alkyl group, and $\gamma$ represents an integer of 0 to 5, with the proviso that when $\gamma$ is at least 2, $R^{e7}$ groups may be different from each other.

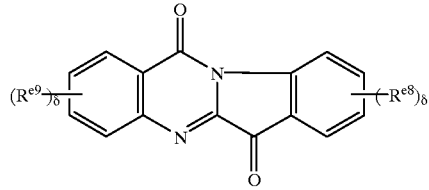
(ET3)

wherein $R^{e8}$ and $R^{e9}$ may be the same or different and represents an alkyl group, $\delta$ represents an integer of 1 to 4, $\epsilon$ represents an integer of 0 to 4, and when $\delta$ and $\epsilon$ are at least 2, the $R^{e8}$ and $R^{e9}$ may be different from each other.

(ET4)

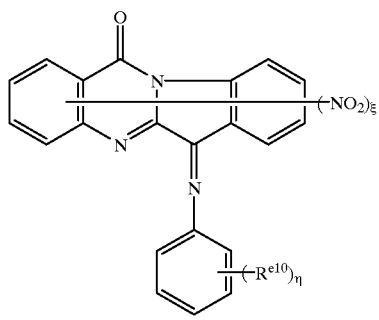

wherein $R^{e10}$ may represent an alkyl group, an aryl group, an aralkyl group, an alkoxy group, a halogenated alkyl group, or a halogen atom, $\zeta$ represents 0 to 4, $\eta$ represents an integer of 0 to 5, with the proviso that when $\eta$ is at least 2, the $R^{e10}$ groups may be different from each other.

(ET5)

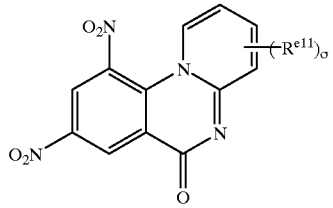

wherein $R^{e11}$ represents an alkyl group, and $\sigma$ represents an integer of 1 to 4, with the proviso that when $\sigma$ is at least 2, the $R^{e11}$ groups may be different from each other.

(ET6)

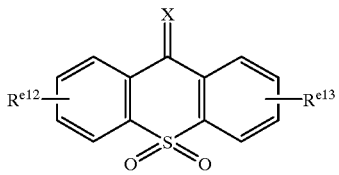

wherein $R^{e12}$ and $R^{e13}$ may be the same or different, and each represents a hydrogen atom, a halogen atom, an alkyl group, an aryl group, an aralkyloxycarbonyl group, an alkoxy group, a hydroxyl group, a nitro group, or a cyano group, X represents an oxygen atom, =N—CN group, or a =C(CN)$_2$ group.

(ET7)

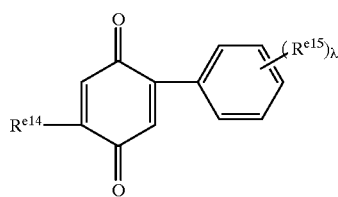

wherein $R^{e14}$ represents a hydrogen atom, a halogen atom, an alkyl group, or a phenyl group which may have a substituent, $R^{e15}$ represents a halongen atom, an alkyl group which may have a substituent, a phenyl group which may have a substituent, an alkoxycarbonyl group, an N-alkylcarbamoyl group, a cyano group or a nitro group and $\lambda$ represents an integer of 0 to 3, with the proviso that when $\lambda$ represents at least 2, the $R^{e15}$ groups may be different from each other.

(ET8)

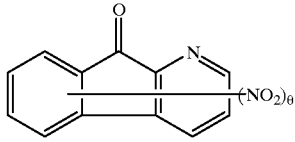

wherein $\theta$ represents an integer of 1 to 2.

(ET9)

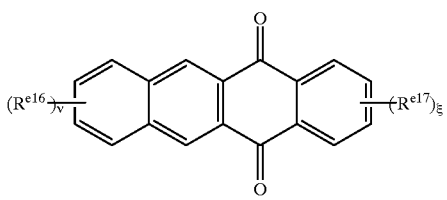

wherein $R^{e16}$ and $R^{e17}$ may be the same or different and each represents a halogen atom, an alkyl group which may have a substituent, a cyano group, a nitro group or an alkoxycarbonyl group, and $\nu$ and $\xi$ represent an integer of 0 to 3, with the proviso that when $\nu$ or $\xi$ is at least 2, the $R^{e16}$ groups and the $R^{e17}$ groups respectively may be different from each other.

(ET10)

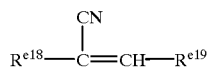

wherein $R^{e18}$ and $R^{e19}$ may be the same or different, and each represents a phenyl group, a polycyclic aromatic group or a heterocyclic group which may have a substituent.

(ET11)

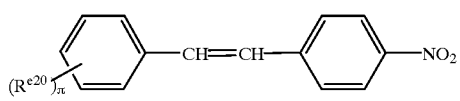

wherein $R^{e20}$ represents an amino group, a dialkylamino group, an alkoxy group, an alkyl group or a phenyl group and $\pi$ represents an integer of 1 to 2, with the proviso that when $\pi$ is at least 2, the $R^{e20}$ groups may be different from each other.

(ET12)

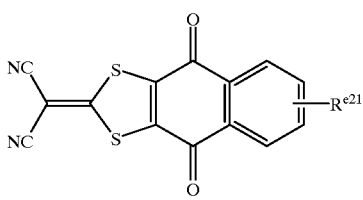

wherein $R^{e21}$ represents a hydrogen atom, an alkyl group, an aryl group, an alkoxy group or an aralkyl group.

(ET13)

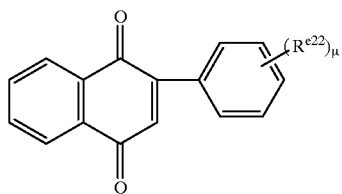

wherein $R^{e22}$ represents a halogen atom, an alkyl group which may have a substituent, a phenyl group which may have a substituent, an alkoxycarbonyl group, an N-alkylcarbamoyl group, a cyano group or a nitro group and $\mu$ represents an integer of 0 to 3, with the proviso that when $\mu$ is at least 2, the $R^{e22}$ groups may be different from each other.

(ET14)

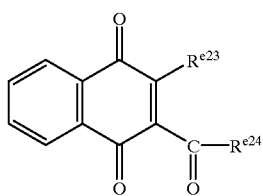

wherein $R^{e23}$ represents an alkyl group which may have a substituent or an aryl group which may have a substituent, and $R^{e24}$ represents an alkyl group which may have a substituent, an aryl group which may have a substituent, or a group shown by —O—$R^{e24a}$ in which $R^{e24a}$ represents an alkyl group which may have a substituent, or an aryl group which may have a substituent.

(ET15)

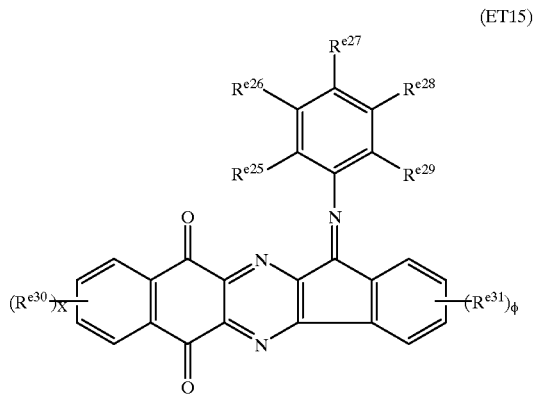

wherein $R^{e25}$, $R^{e26}$, $R^{e27}$, $R^{e28}$, $R^{e29}$, $R^{e30}$ and $R^{e31}$ may be the same or different, each of these groups represents an alkyl group, an aryl group, an aralkyl group, an alkoxy group, a halogen atom or a halogenated alkyl group, $\chi$ and $\phi$ may be the same or different, and represent an integer of 0 to 4.

(ET16)

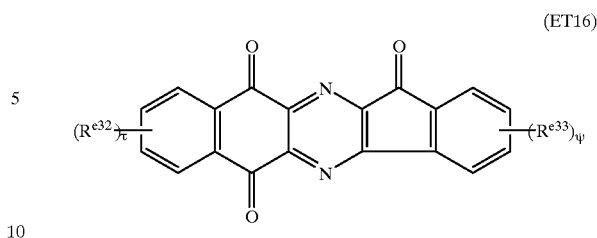

wherein $R^{e32}$ and $R^{e33}$ may be the same or different, and each of these groups represents an alkyl group, an aryl group, an alkoxy group, a halogen atom or a halogenated alkyl group, $\tau$ and $\psi$ may be the same or different, and represent an integer of 0 to 4.

In the above-exemplified electron transporting agents given above, the alkyl group, the aryl group, the alkoxycarbonyl groups, the aralkyl group, the alkoxy group, the halogen atom and the cycloalkyl group may be the same groups as given above.

Examples of the heterocyclic groups include thienyl, furyl, pyrrolyl, pyrrolidinyl, oxazolyl, isooxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino, and thiazolyl. It may be a heterocyclic group fused with an aromatic ring.

Examples of the halogenated alkyl groups include halogenated alkyl groups in which the alkyl group portion has 1 to 6 carbon atoms such as chloromethyl, bromomethyl, fluoromethyl, idodomethyl, 2-chloroethyl, 1-fluoroethyl, 3-chloropropyl, 2-bromopropyl, 1-chloropropyl, 2-chloro-1-methyl-ethyl, 1-bromo-1-methylethyl, 4-iodobutyl, 3-fluorobutyl, 3-chloro-2-methylpropyl, 2-iodo-2-methylpropyl, 1-fluoro-2-methylpropyl, 2-chloro-1,1-dimethylethyl, 2-bromo-1,1-dimethylethyl, 5-bromopentyl and 4-chlorohexyl.

The polycyclic aromatic groups include naphthyl, phenanthryl and anthryl.

The aralkyloxycarbonyl groups include those groups in which the aralkyl portions represent various aralkyl groups mentioned above.

The N-alkylcarbamoyl groups include those groups in which the alkyl portions represent various alkyl groups mentioned above.

The dialkylamino groups include those groups in which the alkyl portions represent various alkyl groups mentioned above. The two alkyl groups substituting the amino group may be the same or different.

The substituent which may be replaced by each group includes a halogen atom, an amino group, a hydroxyl group, a carboxyl group which may be esterified, a cyano group, an alkyl group which has 1 to 6 carbon atoms, an alkoxy group which contains 1 to 6 carbon atoms, or an alkenyl group with 2 to 6 carbon atoms which may contain an aryl group. The subsitution position of the substituent is not particularly limited.

In this invention, in addition to the above-exemplified compounds, conventionally known electron transporting substances may be used. Examples of the conventionally known electron transporting substances include benzoquinone-type compounds, malononitrile, thiopyrane-type compounds, tetracynoethylene, 2, 4, 8-trinitrothioxanthone, dinitrobenzene, dinitroanthracene, dinitroacridine, nitroanthraquinone, dinitroanthraquinone, succinic anhydride, maleic anhydride and dibromomaleic anhydride.

The charge generating agent, the positive hole transporting agent and the binder resin used in the electronphotographic photosensitive material of this invention are as follows.

(Charge Generating Agents)

Examples of the charge generating agents include compounds represented by the general formulae (CG1) to (CG12).

(CG1) Non-metallic phthalocyanine

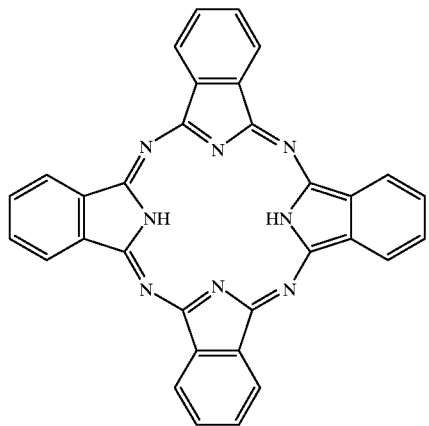
(CG1)

(CG2) Oxotitanylphthalocyanine

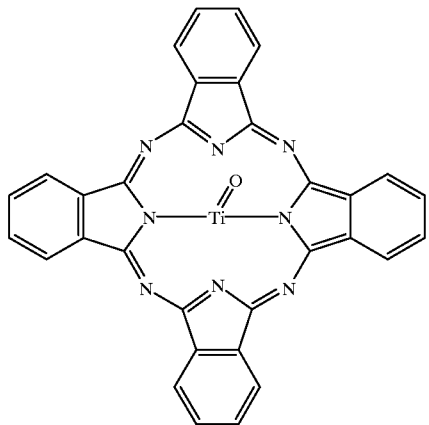
(CG2)

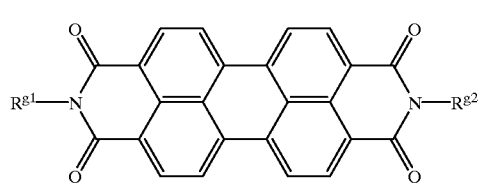
(CG3)

wherein $R^{g1}$ and $R^{g2}$ may be the same or different, and each represents a substituted or unsubstituted, alkyl group, a cycloalkyl group, an aryl group, an alkanoyl group or an aralkyl group having 18 carbon atoms or below.

(CG4) Bisazo pigments

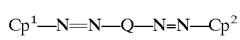
(CG4)

wherein $Cp^1$ and $Cp^2$ are the same or different, each represents a coupler residue, and Q represents formulae expressed by (Q-1) to (Q-8).

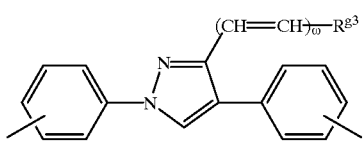
(Q-1)

wherein $R^{g3}$ represents a hydrogen atom, an alkyl group, an aryl group, or a heterocyclic group, the alkyl group, the aryl group and the heterocyclic group may have a substituent, and ω represents 0 or 1.

(Q-2)

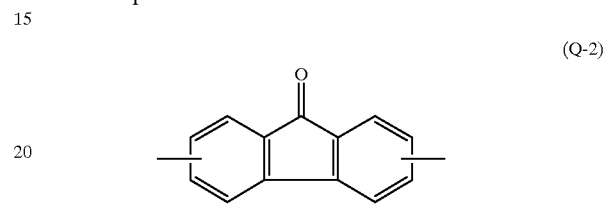

(Q-3)

wherein $R^{g4}$ and $R^{g5}$ are the same or different, and each represents a hydrogen atom, an alkyl group having 1 to 5 carbon atoms, a halogen atom, an alkoxy group, an aryl group, or an aralkyl group.

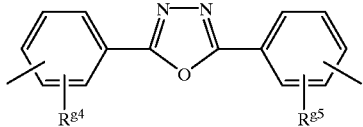
(Q-4)

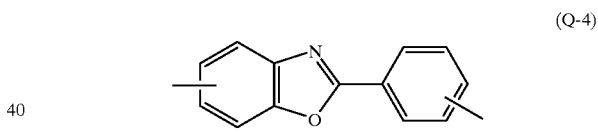
(Q-5)

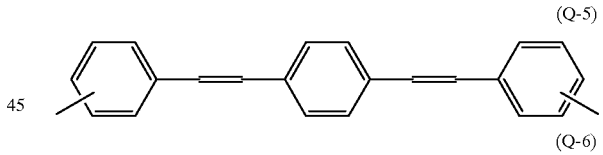
(Q-6)

wherein $R^{g6}$ may represent a hydrogen atom, an ethyl group, a chloroethyl group, or a hydroxyethyl group.

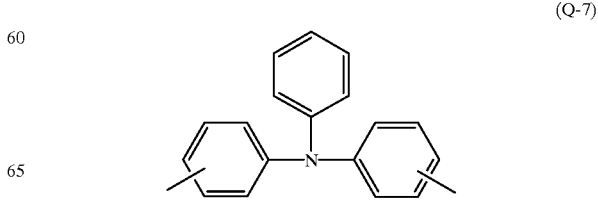
(Q-7)

-continued

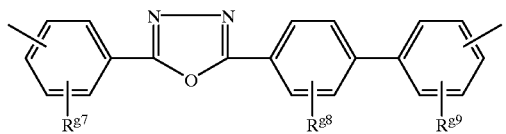
(Q-8)

wherein $R^{g7}$, $R^{g8}$ and $R^{g9}$ may be the same or different, and each represents a hydrogen atom, an alkyl group having 1 to 5 carbon atoms, a halogen atom, an alkoxy group, an aryl group or an aralkyl group.

(CG5) Dithioketopyrrolopyrrole pigments

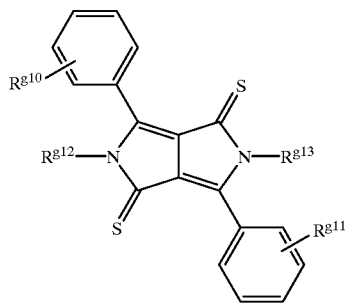
(CG5)

wherein $R^{g10}$ and $R^{g11}$ may be the same or different, each represents a hydrogen atom, an alkyl group, an alkoxy group or a halogen atom, $R^{g12}$ and $R^{g13}$ may be the same or different and each represents a hydrogen atom, an alkyl group or an aryl group.

(CG6) Non-metallic naphthalocyanine pigments

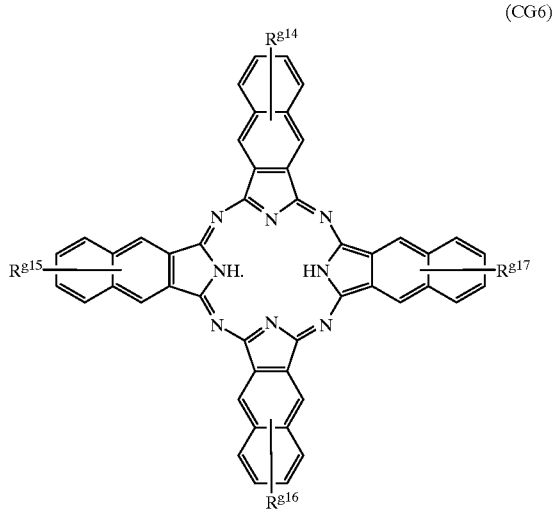
(CG6)

wherein $R^{g14}$, $R^{g15}$, $R^{g16}$ and $R^{g17}$ may be the same or different, and each represents a hydrogen atom, an alkyl group, an alkoxy group or a halogen atom.

(CG7) Non-metallic naphthalocyanine pigments

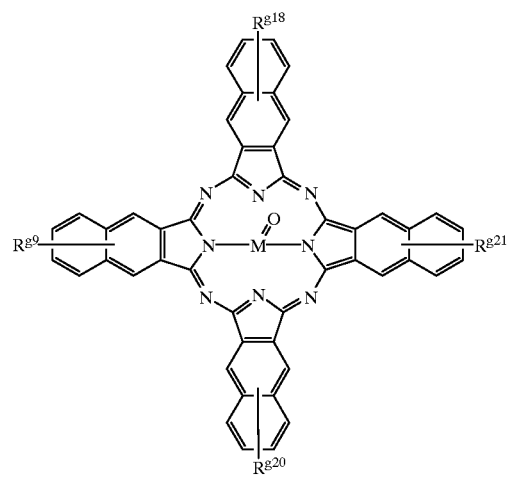
(CG7)

wherein $R^{g18}$, $R^{g19}$, $R^{g20}$ and $R^{g21}$ may be the same or different, each represents a hydrogen atom, an alkyl group, an alkoxy group or a halogen atom, and M represents Ti or V.

(CG8) Squareline pigments

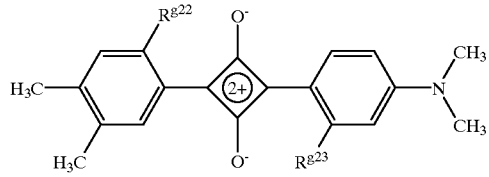
(CG8)

wherein $R^{g22}$ and $R^{g23}$ may be the same or different and each represents a hydrogen atom, an alkyl group, an alkoxy group or a halogen atom.

(CG9) Trisazo pigments

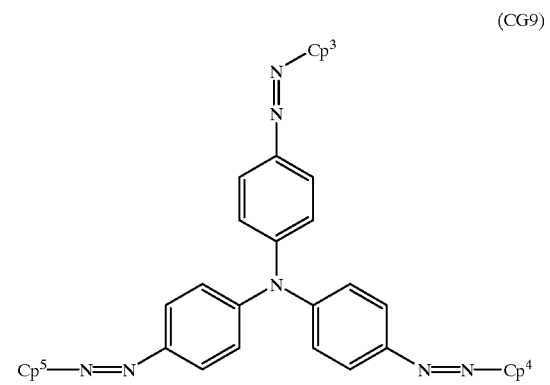
(CG9)

wherein $Cp^3$, $Cp^4$ and $Cp^5$ may be the same or different and represent a coupler residue.

(CG10) Indigo pigments

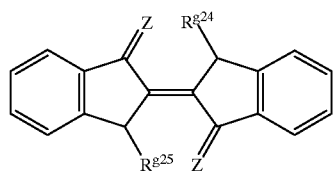
(CG10)

wherein $R^{g24}$ and $R^{g25}$ may be the same or different and each represents a hydrogen atom, an alkyl group or an aryl group, and Z represents an oxygen atom or a sulfur atom.

(CG11) Azulenium pigments

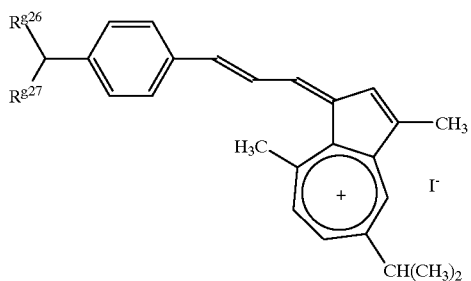
(CG11)

wherein $R^{g26}$ and $R^{g27}$ may be the same or different and each represents a hydrogen atom, an alkyl group or an aryl group.

(CG12) Cyanine pigments

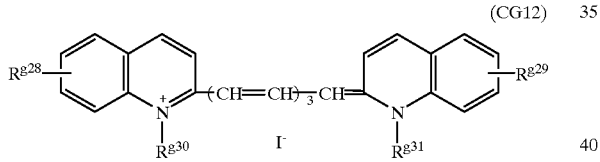
(CG12)

wherein $R^{g28}$ and $R^{g29}$ may be the same or different and each represents a hydrogen atom, an alkyl group, an alkoxy group or a halogen atom, and $R^{g30}$ and $R^{g31}$ may be the same or different and each represents a hydrogen atom, an alkyl grop or an aryl group.

In the above exemplified charge generating agents, the alkyl group may include substituted or unsubstituted alkyl groups having not larger than 18 carbon atoms such as octyl, nonyl, decyl, dodecyl, tridecyl, pentadecyl and octadecyl in addition to the above-mentioned alkyl groups having 1 to 6 carbon atoms.

With regard to the cycloalkyl groups, alkoxy groups, alkanoyl groups, heterocyclic groups, aryl groups, and aralkyl groups, the same groups as mentioned above may be cited.

The substituents which may be substituted on the above groups include halogen atoms, an amino group, a hydroxyl group, a carboxyl group which may be esterified, a cyano group, alkyl groups having 1 to 6 carbon atoms, alkoxy groups having 1 to 6 carbon atoms, and alkenyl groups having 2 to 6 carbon atoms which may have an aryl group.

Examples of the coupler residues represented by $Cp^1$, $Cp^2$, $Cp^3$, $Cp^4$ and $Cp^5$ include groups shown by the general formulae (Cp-1) to (Cp-11) given below.

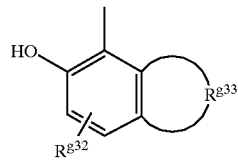
(Cp-1)

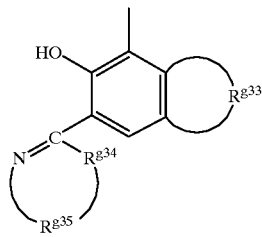
(Cp-2)

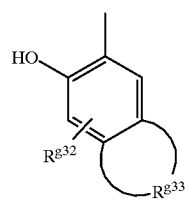
(Cp-3)

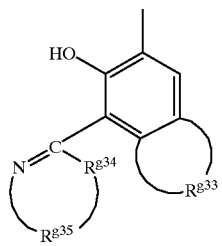
(Cp-4)

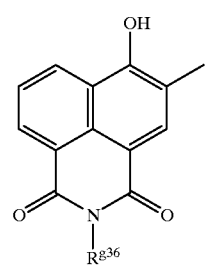
(Cp-5)

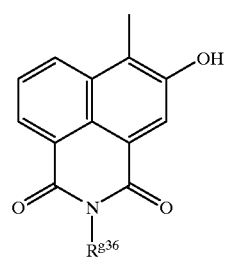
(Cp-6)

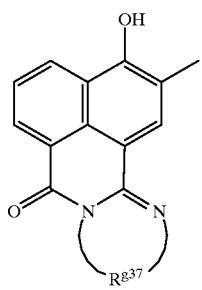
(Cp-7)

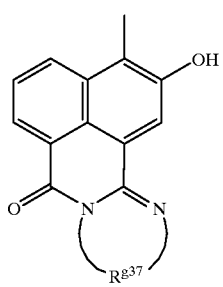
(Cp-8)

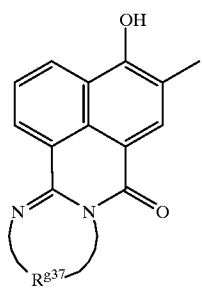
(Cp-9)

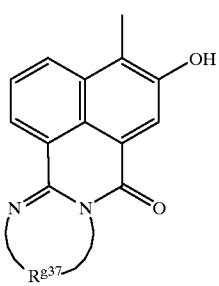
(Cp-10)

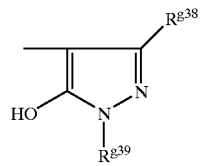
(Cp-11)

In each of the above formulae, $R^{g32}$ represents a carbamoyl group, a sulfamoyl group, an allophanoyl group, an oxamoyl group, an anthraniloyl group, a carbazoyl group, a glycyl group, a hydantoyl group, a phthalamoyl group, or a succinamoyl group. These groups may have a substituent such as a halogen atom, a phenyl group which may have a substituent, a naphthyl group which may have a substituent, a nitro group, a cyano group, an alkyl group, an alkenyl group, a carbonyl group, or a carboxyl group.

$R^{g33}$ represents an atomic grouping required to form an aromatic ring, a polycyclic hydrocarbon or a heterocyclic ring by being fused to the benzene ring. These rings may have the same substituents as described above.

$R^{g34}$ represents an oxygen atom, a sulfur atom or an imino group.

$R^{g35}$ represents a divalent chain hydrocarbon group or an aromatic hydrocarbon group, which may contain the same substituents as described above.

$R^{g36}$ represents an alkyl group, an aralkyl group, an aryl group or a heterocyclic group, which may have the same substituents as described above.

$R^{g37}$ represents an atomic grouping required to form a heterocyclic ring together with a divalent chain hydrocarbon group or aromatic hydrocarbon group, or two nitrogen atoms in the groups (Cp-1) to (Cp-11), and these rings may the same substiutent as described above.

$R^{g38}$ represents a hydrogen atom, an alkyl group, an amino group, a carbamoyl group, a sulfamoyl group, an allophanoyl group, a carboxyl group, an alkoxycarbonyl group, an aryl group or a cyano group, and the groups other than the hydrogen atom may have the same substituent as described above.

$R^{g39}$ represents an alkyl group or an aryl group, and these groups may have the same substituent as above.

Examples of alkenyl groups may include alkenyl groups having 2 to 6 carbon atoms such as vinyl, allyl, 2-butenyl, 3-butenyl, 1-methylallyl, 2-pentenyl, or 2-hexenyl.

In the above $R^{g33}$, examples of the atomic grouping required to form an aromatic ring fused to the benzene ring are alkylene groups having 1 to 4 carbon atoms such as methylene, ethylene, trimethylene and tetramethylene.

The aromatic rings formed by being fused to the benzene ring and the above-mentioned $R^{g33}$ include a naphthalene ring, an anthracene ring, a phenthrene ring, a pyrene ring, a chrysene ring and a naphthacene ring.

In the $R^{g33}$, examples of the atomic grouping required to form a polycyclic hydrocarbon are an alkylene group having 1 to 4 carbon atoms, or a carbazole ring, a benzocarbazole ring, and a dibenzofuran ring.

Furthermore, in $R^{g33}$, examples of the atomic grouping required to form a heterocyclic ring by being fused to the benzene ring include benzofuranyl, benzothiophenyl, indolyl, 1H-indolyl, benzooxazolyl, benzothiazolyl, 1H-indadolyl, benzoimidazolyl, chromenyl, chromanyl, isochromanyl, quinolinyl, isoquinolinyl, cinnolinyl, phthalazinyl, quinazolinyl, quinoxalinyl, dibenzofuranyl, carbazolyl, xanthenyl, acridinyl, phenanthridinyl, phenazinyl, phenoxazinyl and thianthrenyl.

Examples of the aromatic heterocyclic groups formed by the condensation of the $R^{g33}$ and the benzene ring include thienyl, furyl, pyrrolyl, oxazolyl, isooxazolyl, thiazolyl, isothiazolyl, imidazolyl, pyrazolyl, triazolyl, tetrazolyl, pyridyl and thiazolyl. They may be heterocyclic ring groups fused to other aromatic rings, such as benzofuranyl, benzoimidazolyl, benzooxazolyl, benzothiazolyl and quinolyl.

In $R^{g35}$ and $R^{g37}$, the divalent chain hydrocarbon groups include ethylene, trimethylene, and tetramethylene. Examples of the divalent aromatic hydrocarbon groups include phenylene, naphthylene and phenanthrylene.

In $R^{g36}$ examples of the heterocyclic ring include pyridyl, pyrazyl, thienyl, pyranyl and indolyl.

In $R^{g37}$, examples of the atomic groupings required to form heterocyclic rings together with two nitrogen atoms are phenylene, naphthylene, phenanthrylene, ethylene, trimethylene and tetramethylene.

Examples of the aromatic heterocyclic rings formed from $R^{g37}$ and two nitrogen atoms include benzoimidazole, benzo

[f]benzoimidazole, dibenzo[e,g]-benzoimidazole and benzopyrimidine. These groups may have the same substituents as mentioned above.

In $R^{38}$, examples of the alkoxycarbonyl groups include methoxycarbonyl, ethoxycarbonyl, propoxycarbonyl and butoxycarbonyl groups.

In this invention, in addition to the above-illustrated charge generating agents, conventionally known charge generating agents may be used. Examples of the conventionally known charge generating agents include powders of inorganic photoconductor materials such as selenium, selenium-tellurium, selenium-arsenic, cadmium sulfide and amorphous silicon; pyrylium salts; anthanthrone-type pigments; triphenylmethane-type pigments; thren-type pigments; toluidine-type pigments; pyrazoline-type pigments; and quinacridone-type pigments.

The above-illustrated charge generating agents may be used singly or as a mixture consisting of at least two agents so that a predetermined wavelength may have in a desired region.

Among the above-exemplified charge generating agents given above, since especially digital optical system-image forming apparatuses such as a laser beam printer or a facsimile require a photosensitive material having sensitivity in a wavelength region of at least 700 nm, non-metallic phthalocyanine represented by the general formula (CG1) or phthalocyanine-type pigments such as oxotitanyl phthalocyanine represented by the general formula (CG2) are preferably used. The crystal forms of the phthalocyanine-type pigments are not particularly limited, and various types may be used.

On the other hand, since analog optical system-image forming apparatuses such as electrostatic copying machines using a white light source such as a halogen lamp require a photosensitive material having sensitivity in a visible region, perylene pigments represented by the general formula (CG3) or bisazo pigments represented by the general formula (CG4) are preferably used.

<Positive hole transporting agents>

Positive hole transporting agents may be various compounds having a high positive hole transportability, for example, the compounds represented by (HT1) to (HT13).

(HT1)

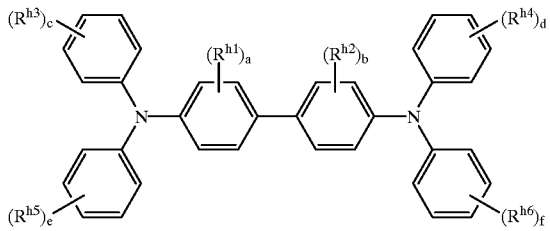

wherein $R^{h1}$, $R^{h2}$, $R^{h3}$, $R^{h4}$, $R^{h5}$ and $Rh^6$ may be the same or different and each represents a halogen atom, an alkyl group which may have a substituent, an alkoxy group which may have a substituent, or an aryl group which may have a substituent, and a and b may be the same or different and represent an integer of 0 to 4, c, d, e and f may be the same or different and represent an integer of 0 to 5, with the proviso that when a, b, c, d, e or f are at least 2, $R^{h1}$, $R^{h2}$, $R^{h3}$, $R^{h4}$, $R^{h5}$ and $Rh^6$ may be different.

(HT2)

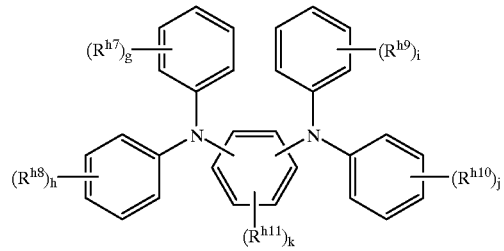

wherein $R^{h7}$, $R^{h8}$, $R^{h9}$, $R^{h10}$ and $R^{h11}$ may be the same or different and each represents a halogen atom, an alkyl group which may have a substituent, an alkoxy group which may have a substituent or an aryl group which may have a substituent, g, h, i and j may be the same or different and represent an integer of 0 to 5, and k represents an integer of 0 to 4, with the proviso that when g, h, i, j or k is at least 2, $R^{h7}$, $R^{h8}$, $R^{h9}$, $R^{h10}$ and $R^{h11}$ may be different from each other.

(HT3)

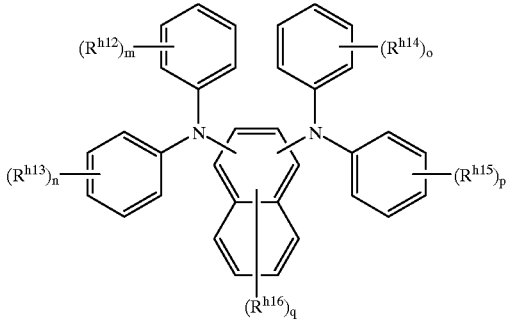

wherein $R^{h12}$, $R^{h13}$, $R^{h14}$ and $R^{h15}$ may be the same or different and each represents a halogen atom, an alkyl group which may have a substituent, an alkoxy group which may have a substituent or an aryl group which may have a substituent, $R^{h16}$ represents a halogen atom, a cyano group, a nitro group, an alkyl group which may have a substituent, an alkoxy group which may have a substituent or an aryl group which may have a substituent, m, n, o and p may be the same or different from each other and represent an integer of 0 to 5, and q represents an integer of 1 to 6, with the proviso that when m, n, o, p or q are at least 2, $R^{h12}$, $R^{h13}$, $R^{h14}$, $R^{h15}$ and $R^{h16}$ may be different from each other.

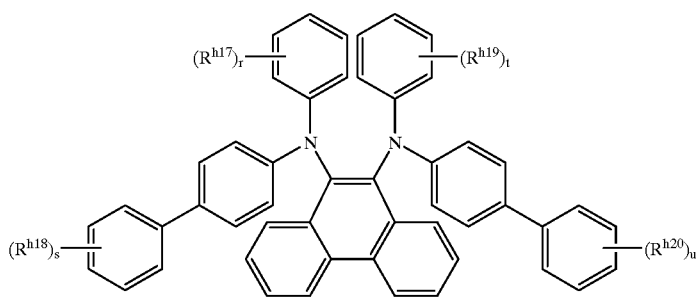
(HT4)

wherein $R^{h17}$, $R^{h18}$, $R^{h19}$ and $R^{h20}$ may be the same or different from each other and each represents a halogen atom, an alkyl group which may have a substituent, an alkoxy group which may have a substituent or an aryl group which may have a substituent, r, s, t and u may be the same or different and represent an integer of 0 to 5, with the proviso that when r, s, t or u represents at least 2, $R^{h17}$, $R^{h18}$, $R^{h19}$ and $R^{h20}$ may be different from each other.

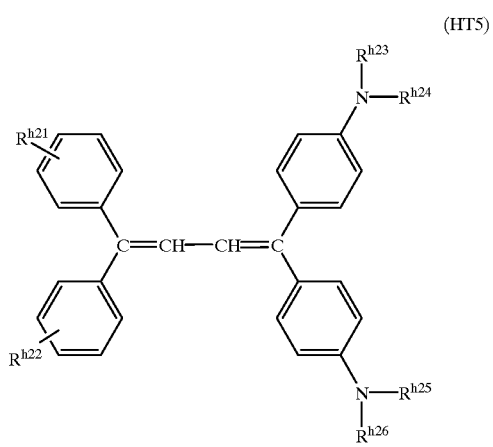
(HT5)

wherein $R^{h21}$ and $R^{h22}$ may be the same or different and each represents a hydrogen atom, a halogen atom, alkyl group or alkoxy group, $R^{h23}$, $R^{h24}$, $R^{h25}$ and $R^{h26}$ may be the same or different from each other and each represents a hydrogen atom, a halogen atom, an alkyl group or an alkoxy group.

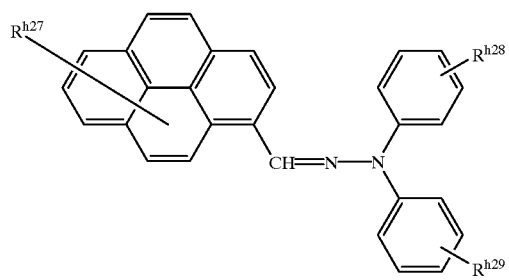
(HT6)

wherein $R^{h27}$, $R^{h28}$ and $R^{h29}$ may be the same or different from each other and each represents a hydrogen atom, a halogen atom, an alkyl group or an aryl group.

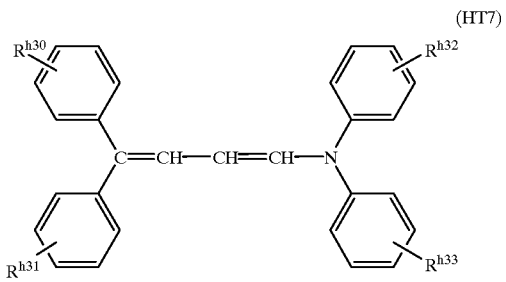
(HT7)

wherein $R^{h30}$, $R^{h31}$, $R^{h32}$ and $R^{h33}$ may be the same or different from each other and each represents a hydrogen atom, a halogen atom, an alkyl group or an alkoxy group.

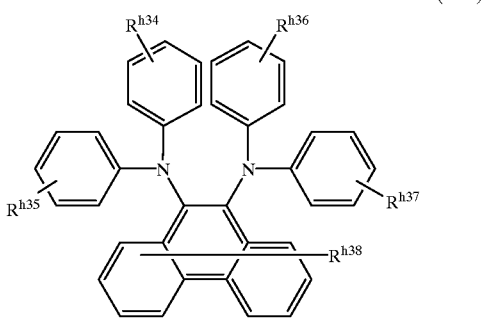
(HT8)

wherein $R^{h34}$, $R^{h35}$, $R^{h36}$, $R^{h37}$ and $R^{h38}$ may be the same or different from each other and each represents a hydrogen atom, a halogen atom, an alkyl group or an alkoxy group.

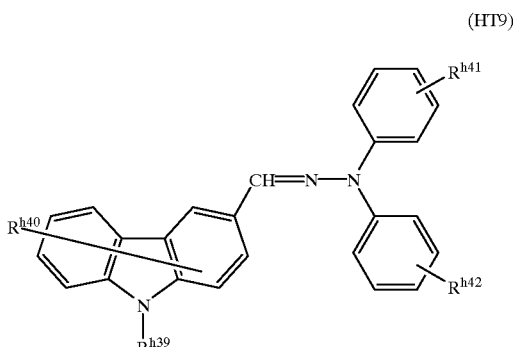
(HT9)

wherein $R^{h39}$ represents a hydrogen atom or an alkyl group, and $R^{h40}$, $R^{h41}$ and $R^{h42}$ may be the same or different and each represents a hydrogen atom, a halogen atom, an alkyl group or alkoxy group.

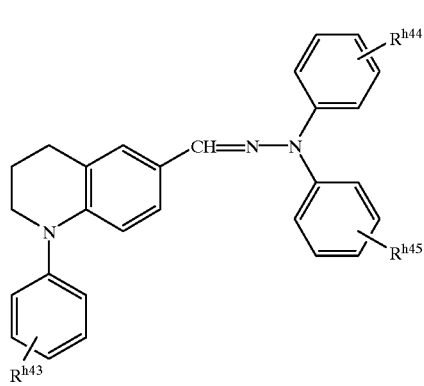

(HT10)

wherein $R^{h43}$, $R^{h44}$ and $R^{h45}$ may be the same or different from each other and each represents a hydrogen atom, a halogen atom, an alkyl group or an alkoxy group.

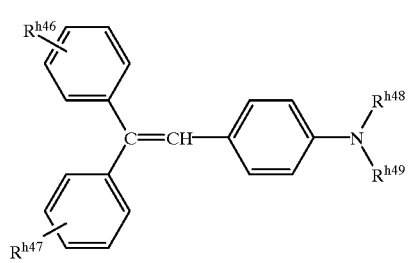

(HT11)

wherein $R^{h46}$ and $R^{h47}$ may be the same or different and each represents a hydrogen atom, a halogen atom, an alkyl group which may have a substituent or an alkoxy group which may have a substituent, and $R^{h48}$ and $R^{h49}$ may be the same or different from each other and each represents a hydrogen atom, an alkyl group which may have a substituent or an aryl group which may have a substituent.

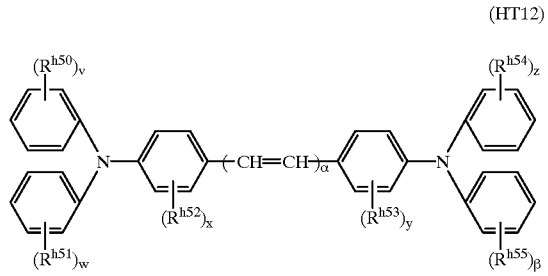

(HT12)

wherein $R^{h50}$, $R^{h51}$, $R^{h52}$, $R^{h53}$, $R^{h54}$ and $R^{h55}$ may be the same or different from each other and each represents an alkyl group which may have a substituent, an alkoxy group which may have a substituent or an aryl group which may have a substituent, $\alpha$ represents an integer of 1 to 10, v, w, x, y, z and $\beta$ may be the same or different from each other and represent an integer of 0 to 2, with the proviso that when v, w, x, y, z or $\beta$ represents 2, $R^{h50}$, $R^{h51}$, $R^{h52}$, $R^{h53}$, $R^{h54}$ and $R^{h55}$ may be different from each other.

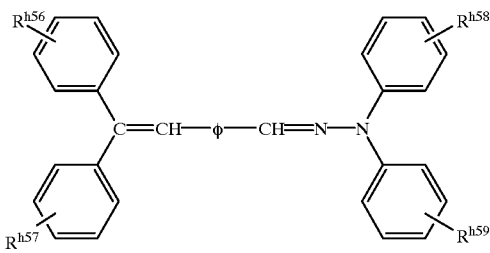

(HT13)

wherein $R^{h56}$, $R^{h57}$, $R^{h58}$ and $R^{h59}$ may be the same or different and each represents a hydrogen atom, a halogen atom, an alkyl group or an alkoxy group, and $\phi$ represents a group of ($\phi$-1), ($\phi$-2) or ($\phi$-3) shown below

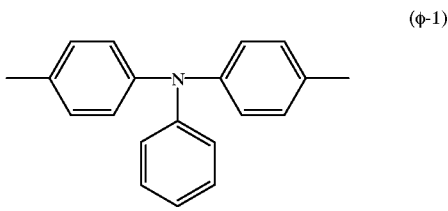

($\phi$-1)

($\phi$-2)

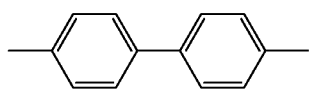

($\phi$-3)

In the above-illustrated positive hole transporting agents, the alkyl group, alkoxy group, halogen atom, aryl group and aralkyl group may include the same groups as given above.

The substituents which may be substituted by the above groups include halogen atoms, amino group, hydroxyl group, carboxyl group which may be esterified, a cyano group, alkyl groups which have 1 to 6 carbon atoms, alkoxy groups having 1 to 6 carbon atoms, and alkenyl groups having 2 to 6 carbon atoms which may have an aryl group. The substitution positions of the substituent may not particularly be limited.

In the present invention, in addition to the above-illustrated examples, conventionally known positive hole transporting substances, for example, oxadiazole-type compounds such as 2,5-di(4-methylaminophenyl)-1, 3, 4-oxadiazole, styryl-type compounds such as 9-(4-diethylaminostyryl)anthracene, carbazole-type compounds such as polyvinylcarbazole, organic polysilane compounds, pyrazoline-type compounds such as 1-phenyl-3-(p-dimethylaminophenyl)pyrazoline, nitrogen-containing cyclic compounds such as hydrazone-type compounds, triphenylamine-type compounds, indole-type compounds, oxazole-type compounds, isooxazole-type compounds, thiazole-type compounds, thiadiazole-type compounds, imidazole-type compounds, pyrazole-type compounds and triazole-type compounds, and condensed polycyclic compounds may be used.

In the present invention, the positive hole transporting agents may be used singly or as mixtures of at least two agents. When a positive hole transporting agent having film formability such as polyvinylcarbazole is used, the binder resin is not always necessary.

In the present invention, the positive hole transporting agents having an ionization potential (Ip) of 4.8 to 5.6 eV are preferably used. The positive hole transporting agents having a mobility of at least $1 \times 10^{-6} m^2/V$ second at a field strength of $3 \times 10^5$ V/cm are more preferred.

By using positive hole transporting agents having an ionization potential within the above range, the residual potential can be further decreased, and sensitivity is increased. The reasons for it are not always clear, but are assumed as follows.

The ease of injection of a charge from a charge generating agent to a positive hole transporting agent relates intimately to the ionization potential of the positive hole transporting agent, and when the ionization potential of the positive hole transporting agent is larger than the above-mentioned range, the degree of injection of a charge from the charge generating agent to the positive hole transporting agent becomes low or the degree of donation and receiving of the positive hole between the positive hole transporting agents becomes low, and therefore a lowering of sensitivity is considered to take place. On the other hand, in a system in which the positive hole transporting agent and the electron transporting agent are present together, one must take care of an interaction between both agents, more specifically one must take care of the formation of a charge transfer complex. When such a complex is formed between both agents, the positive hole and the electron take place re-bonding, and as a whole, the degree of mobility of a charge is lowered. When the ionization potential of the positive hole transporting agent is smaller than the above range, there is a large inclination of forming a complex between the positive hole transporting agent and the electron transporting agent, and the electron and positive hole take place rebonding with the result that the apparent quantum yield is lowered, and it is considered to be linked with a decrease of sensitivity.

When a bulky group exists in the electron transporting agent, its steric hindrance can suppress the formation of a charge transfer complex. Accordingly, in naphthoquinone derivative (1) used as the electron transporting agent in this invention, it is preferred to introduce as bulky substituents as possible.

A specific example of the positive hole transporting agent preferably used in this invention includes a compound of the formula (HT1-1) belonging to a benzidine derivative of the above general formula (HT1).

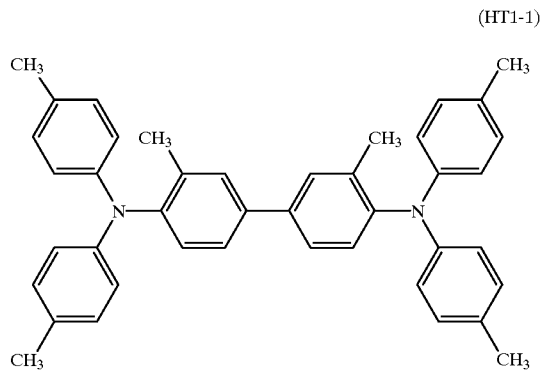

(HT1-1)

<Binder resins>

Various resins conventionally used in a photosensitive layer may be used as binder resins for dispersing various components. Examples of the binder resins include thermoplastic resins such as styrene-type polymers, styrene-butadiene copolymers, styrene-acrylonitrile copolymers, styrene-maleic acid copolymers, acrylic copolymers, styrene-acrylic acid copolymers, polyethylene, ethylene-vinyl acetate copolymers, chlorinated polyethylene, polyvinyl chloride, polypropylene, ionomers, vinyl chloride-vinyl acetate copolymers, polyesters, alkyd resins, polyamides, polyurethanes, polycarbonates, polyallylate, polysulfones, diallyl phthalates, ketone resins, polyvinylbutyral resins, polyether resins and polyester resins; thermosetting resins such as silicone resins, epoxy resins, phenolic resins, urea resins, melamine resins and other crosslinkable thermosetting resins; and photo-curable resins such as epoxy acrylate and urethane-acrylate. These binder resins may be used singly or as mixtures of at least two resins. Preferred resins include styrene-type polymers, acrylic-type polymers, styrene-acrylic type copolymers, polyesters, alkyd resins, polycarbonates and polyallylate.

The process for producing the electrophotographic polysensitive material of this invention will be described.

To obtain a single layer type electrophotographic photosensitive material, a predetermined electron transporting agent together with a charge generating agent, a positive hole transporting agent and a binder resin is dissolved or dispersed in a suitable solvent, and the resulting coating solution is coated on an electroconductive substrate by a coating means, and the coating solution may be dried.

In the single-type photosensitive material, 0.1 to 50 parts by weight, preferably 0.5 to 30 parts by weight, of a charge generating agent, 5 to 100 parts by weight, preferably 10 to 80 parts by weight, of an electron transporting agent, 5 to 500 parts by weight, preferably 25 to 200 parts by weight, of a positive hole transporting agent are compounded per 100 parts by weight of the binder resin. The total amounts of the positive hole transporting agent and the electron transporting agent are 20 to 500 parts by weight, preferably 30 to 200 parts by weight, per 100 parts by weight of the binder resin. When an electron acceptor is included into the single layer-type photosensitive layer, it is suitable to compound 0.1 to 40 parts by weight, preferably 0.5 to 20 parts by weight, of the electron acceptor per 100 parts by weight of the binder resin.

The thickness of the single layer-type photosensitive layer is 5 to 100 µm, preferably 10 to 50 µm.

To obtain a single layer-type electrophotographic photosensitive material, a charge generating layer containing a charge generating agent is formed on an electroconductive substrate by such a means as evaporation or coating, then coating a solution containing an electron transporting agent and a binder resin on the charge generating layer, and drying the coated layers to form a charge transporting layer.

In the laminated-type photosensitive material, the charge generating agent forming a charge generating agent and the binder resin may be used in various proportions. It is suitable to compound 5 to 1000 parts by weight of the charge generating agent, preferably 30 to 500 parts by weight, per 100 parts by weight of the binder resin. When an electron acceptor is included in the charge generating layer, it is suitable to compound 0.1 to 40 parts by weight, preferably 0.5 to 20 parts by weight, of the electron acceptor per 100 parts by weight of the binder resin. When it is desired to include the electron transporting agent into the charge generating layer, it is suitable to compound 0.5 to 50 parts by weight, preferably 1 to 40 parts by weight, of the electron transporting agent per 100 parts by weight of tie binder resin.

The electron transporting agent constituting the charge transporting layer and the binder resin may be used in various proportions within a range which does not impede the transporting of the charge and within a range which does not cause crystallization. To easily transport the charge generated by light irradiation in the charge generating layer, it is suitable to compound 10 to 500 parts by weight preferably 25 to 100 parts by weight of the electron transporting agent to 100 parts by weight of the binder resin. When an electron acceptor compound is included into the charge transporting layer, it is suitable to compound the electron acceptor in an amount of 0.1 to 40 parts by weight, preferably 0.5 to 20 parts by weight, per 100 parts by weight of the binder resin.

The thickness of the photosensitive material of the laminated-type may be such that the charge generating layer has a thickness of about 0.01 to 5 $\mu$m, preferably about 0.1 to 3 $\mu$m, and the charge transporting layer has a thickness of 2 to 100 $\mu$m, preferably about 5 to 50 $\mu$m.

In the single-type photosensitive material, a barrier layer which does not impede the characteristics of the photosensitive material may be formed between the electroconductive substrate and the photosensitive layer and in the laminated-type photosensitive material, such a barrier layer may be formed between the electroconductive substrate and the charge generating layer, or between the electroconductive substrate and the electron transporting layer, or between the charge generating layer and the charge transporting layer. Furthermore, a protective layer may be formed on the surface of the photosensitive material.

In the photosensitive materials of the single layer-type and the laminated-type, various known additives, including deterioration preventive agents such as antioxidants, radical scavengers, single state quenchers, ultraviolet absorbents, softening agents, plasticizers, surface modifiers, extenders, thickeners, dispersion stabilizers, waxes, acceptors and donors, may be compounded. To increase the photosensitivity of the photosensitive material, known sensitizers such as terphenyl, halonaphthoquinones and acenaphthylene may be conjointly used with charge generating agents.

Various electron transporting agents having high electron transportability may be included in the photosensitive layer together with the naphthoquinone derivative expressed by the general formula (1) given above.

The electroconductive substrate used in the photosensitive material of this invention may be various materials having electroconductivity. They may include single metals such as aluminum, iron, copper, tin, platinum, silver, vanadium, molybdenum, chromium, cadmium, titanium, nickel, palladium, indium, stainless steel, and brass; plastic materials on which the above metals are vacuum evaporated or laminated; and glasses coated with aluminum iodide, tin oxide and indium oxide.

The electroconductive substrates may be sheet-like or drum-like. The substrates themselves may have electroconductivity, or the surfaces of the substrates may have electroconductivity. In use, the electroconductive substrates should preferably have sufficient mechanical strength.

The photosensitive material of this invention may be produced by dissolving or dispersing a resin composition containing various components in a solvent and coating the resulting coating solution on an electroconductive substrate and drying the coating solution.

The above illustrated charge generating agent, the charge transporting agent and the binder resin and a suitable solvent are dispersed and mixed by using a roll mill, a ball mill, an attriter, a paint shaker, or an ultrasonic disperser to prepare a coating solution, and coating the resulting coating solution and the drying it.

Various solvents may be used as the solvent to prepare the coating solution. Examples of the solvents include alcohols such as methanol, ethanol, isopropanol and butanol, aliphatic hydrocarbons such as n-hexane, octane and cyclohexane, aromatic hydrocarbons such as benzene, toluene and xylene, halogenated hydrocarbons such as dichloromethane, dichloroethane, carbon tetrachloride and chlorobenzene, ethers such as dimethyl ether, diethyl ether, tetrahydrofuran, ethyleneglycoldimethylether and diethyleneglycoldimethylether, ketones such as acetone, methylethylketone and cyclohexanone, esters such as ethyl acetate and methyl acetate, and dimethylformaldehyde, dimethylformamide and dimethylsulfoxide. These solvents may be used singly or mixtures of at least two types.

To improve the dispersibility of the charge transporting material or the charge generating material and the smoothness of the surface of the photosensitive layer, a surface active agent and a levelling agent may be used.

EXAMPLES

The following Synthesis Examples and Examples will illllustrate the electrophotographic photosensitive materials of this invention.

Synthesis Example 1

[Synthesis of a naphthoquinone derivative expressed by the formula (1-1)]

A 200 ml flask containing two mouths was charged with 2.0 g (3.6 mmol) of a naphthoquione derivative (4-1) in which $R_1$ is a phenyl group, and after replacing an argon, 0.42 g (3.1 mmol) of aldehyde (5-1)/70 ml of toluene were added, and the mixture was refluxed by heating for 3 hours. After cooling, toluene was distilled off, and the product was purified by columun chromatography to give the final product. (Yielded amount 1.8 g, the yield 72.5%). Melting point at least 300° C.

Figure 2:
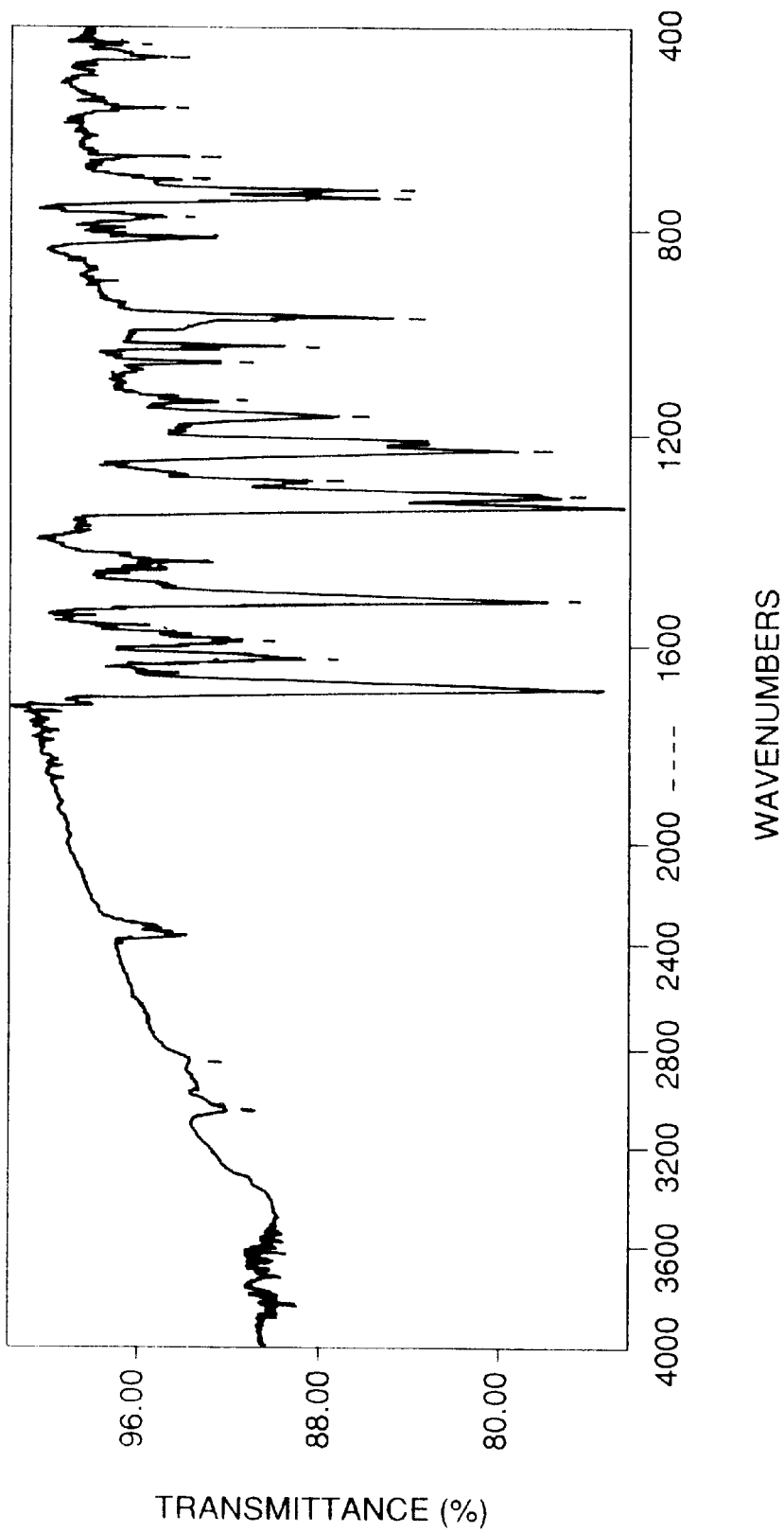
FIG. 2 shows a graph showing the IR spectrum of a naphthoquinone derivative (1-1) of this invention.
Figure 3:
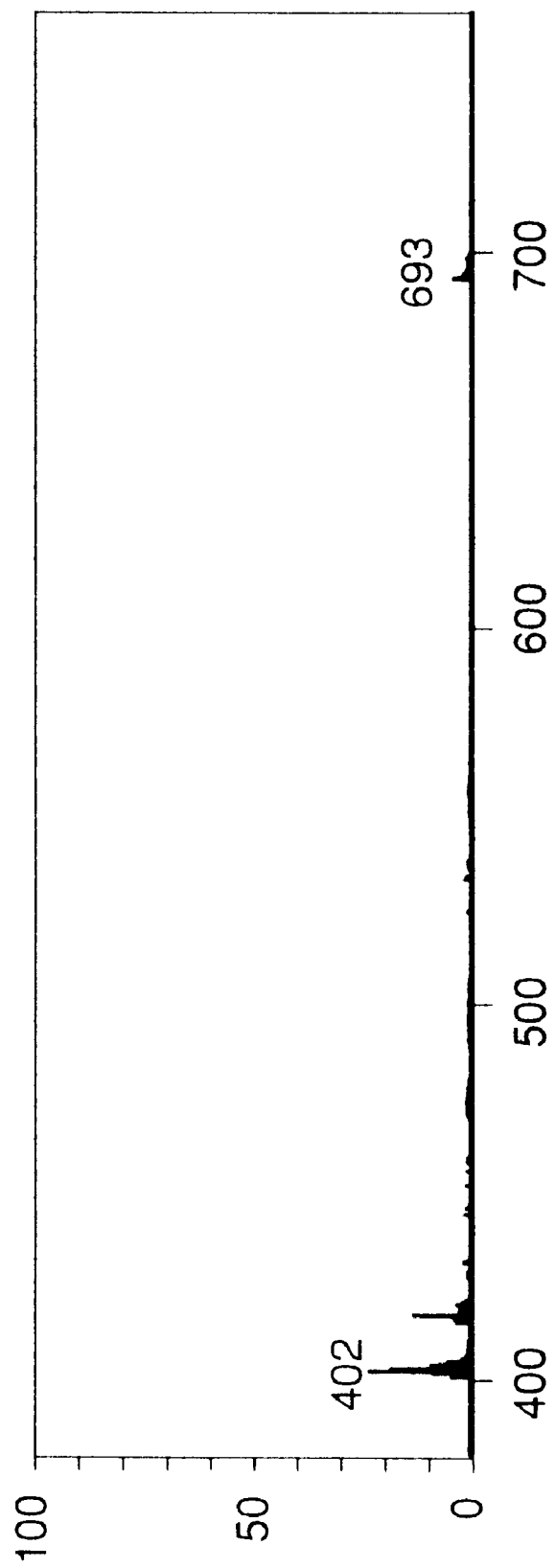
FIG. 3 shows a graph showing the MS specrum of the naphthoquinone derivative (1-1) of this invention.

The IR spectrum of the product is shown in FIG. 2, and its MS spectrum is shown in FIG. 3.

The reaction formula of the above reaction is shown below.

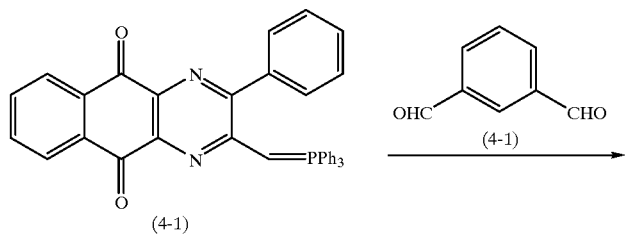

-continued

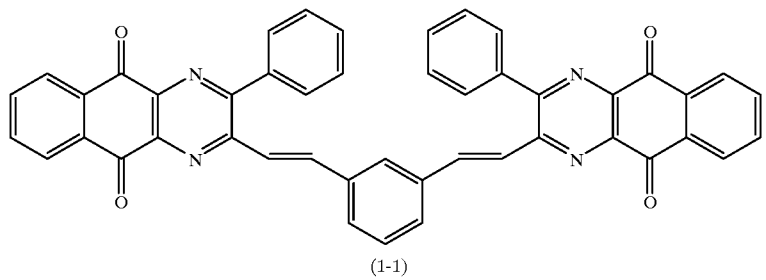

(1-1)

Synthesis Example 2

[Synthesis of a naphthoquinone derivative represented by the formula (1-2)]

The same reaction was carried out except that instead of the formula (5-1), 8.1 mmols of (5-2) was used to give the above identified compound was obtained (yielded amount 1.9 g, yield 53.8%). Melting point 242 to 244° C.

Figure 4:
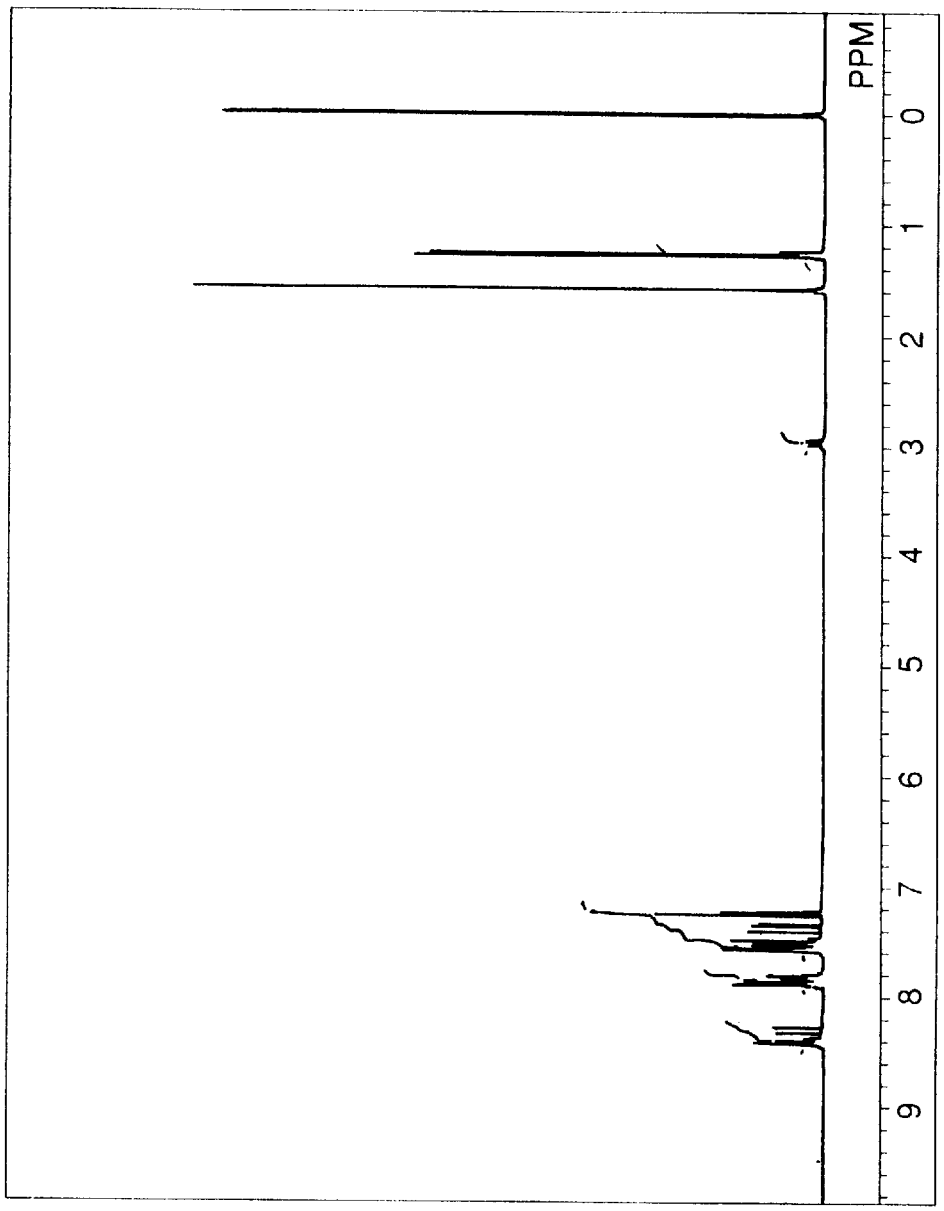
FIG. 4 shows a graph showing the 1H-NMR spectrum of a naphthoquinone derivative (1-2) of this invention.
Figure 5:
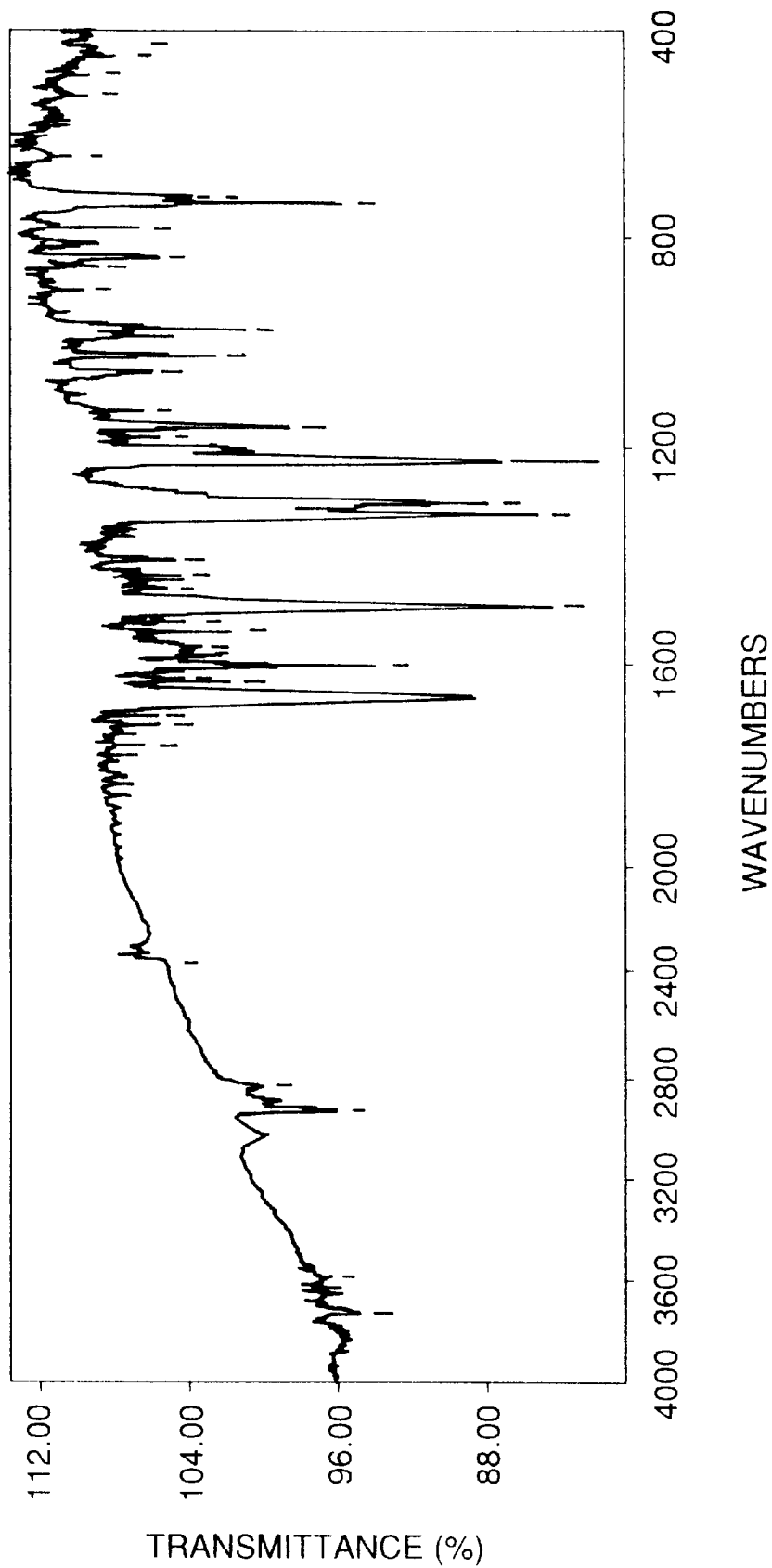
FIG. 5 shows a graph showing the IR spectrum of the naphthoquinone derivative (1-2) of this invention.
Figure 6:
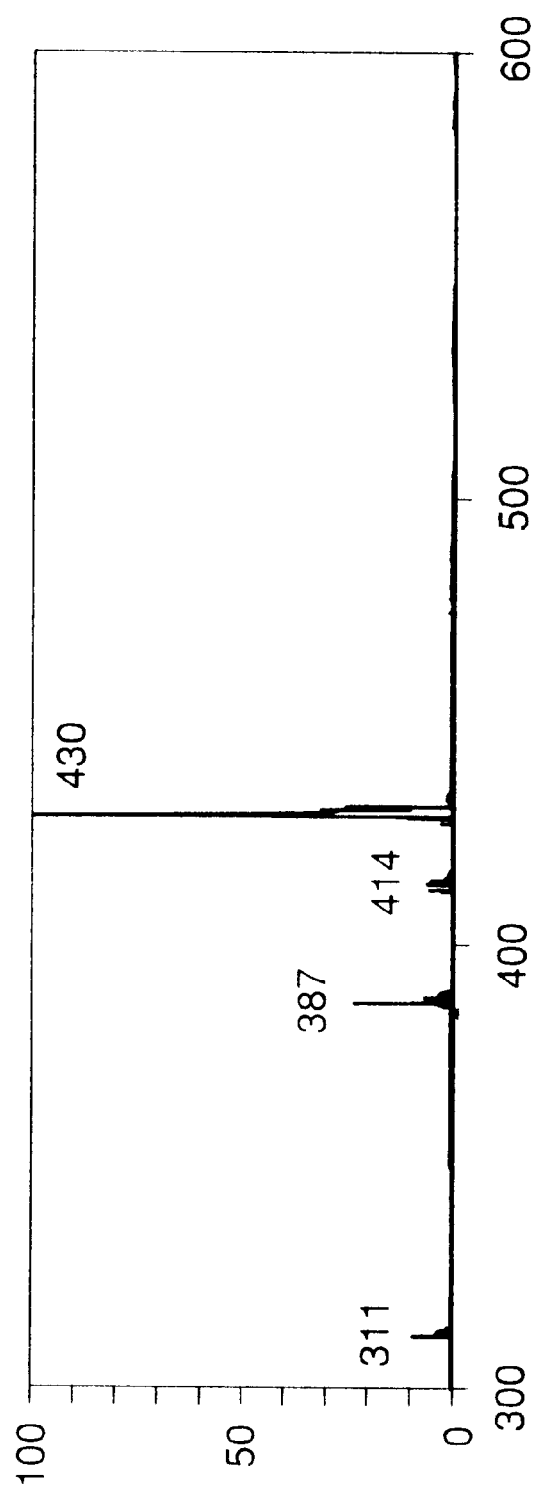
FIG. 6 shows a graph showing the MS spectrum of the naphthoquinone derivative (1-2) of this invention.

The IH-NMR spectrum of the product is shown in FIG. 4, its IR spectrum is shown in FIG. 5, and its MS spectrum is shown in FIG. 6.

The compound (5-2) is shown below.

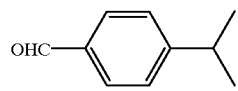

(5-2)

Synthesis Example 3

[Synthesis of a naphthoquinone derivative expressed by the formula (1-3)]

The same Synthesis Example 1 was carried out except that instead of the formula (5-1), 3.6 mmol of (5-3) was used to give the below-mentioned compound (yielded amount 1.5 g, yield 92.1%). Melting point 224 to 227° C.

Figure 7:
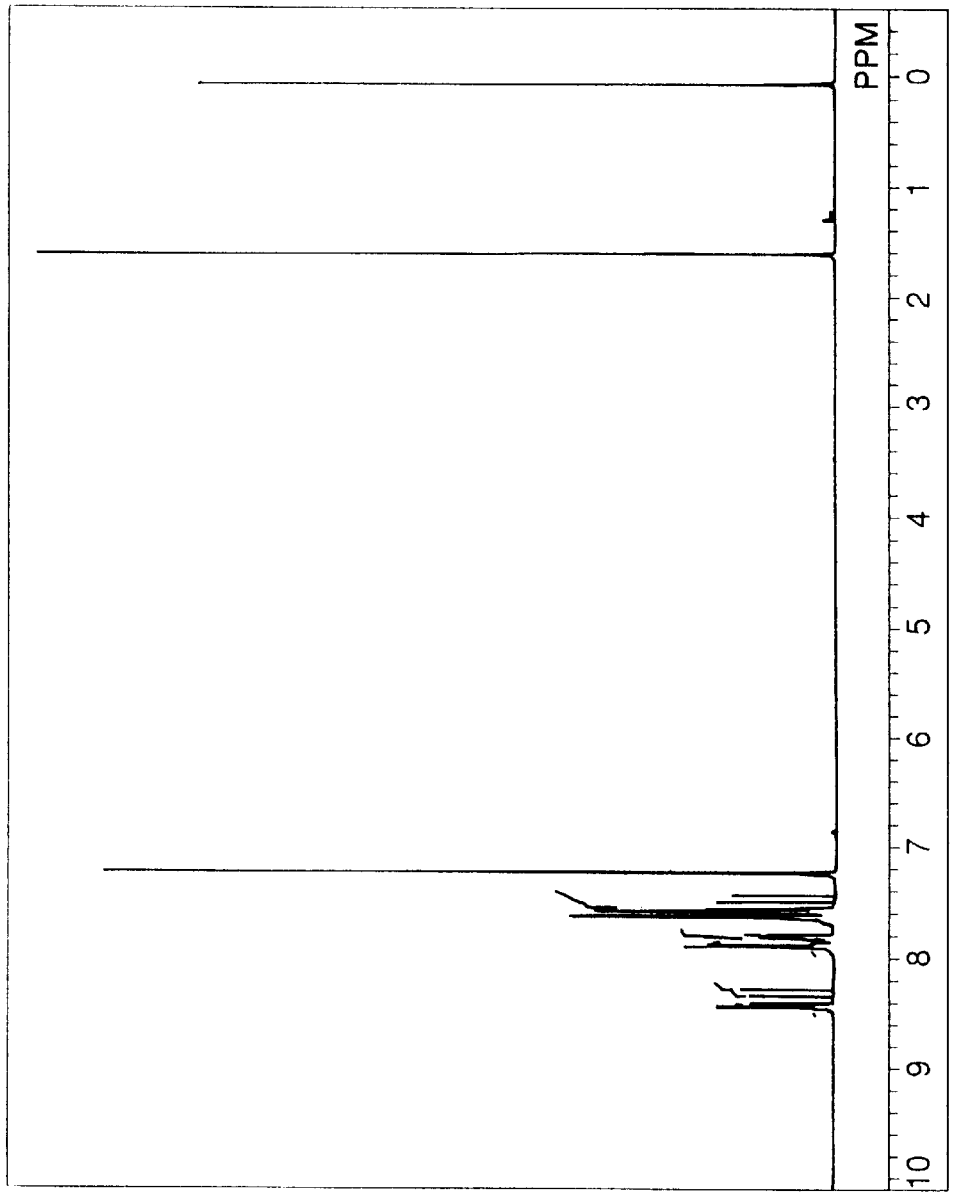
FIG. 7 shows a graph showing the 1H-NMR spectrum of a naphthoquinone derivative (1-3) of this invention.

The 1H-NMR spectrum of the product is shown in FIG. 7.

The compound (5-3) is shown below.

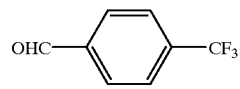

(5-3)

Synthesis Example 4

[Synthesis of a naphthoquinone derivative expressed by the formula (1-4)]

The same Synthesis Example 1 was carried out except that instead of the formula (5-1), (5-4) was used in an amount of 3.6 mmol to give the below-mentioned compound (the yielded amount 1.4 g, yield 87.9%). Melting point 228 to 231° C.

Figure 8:
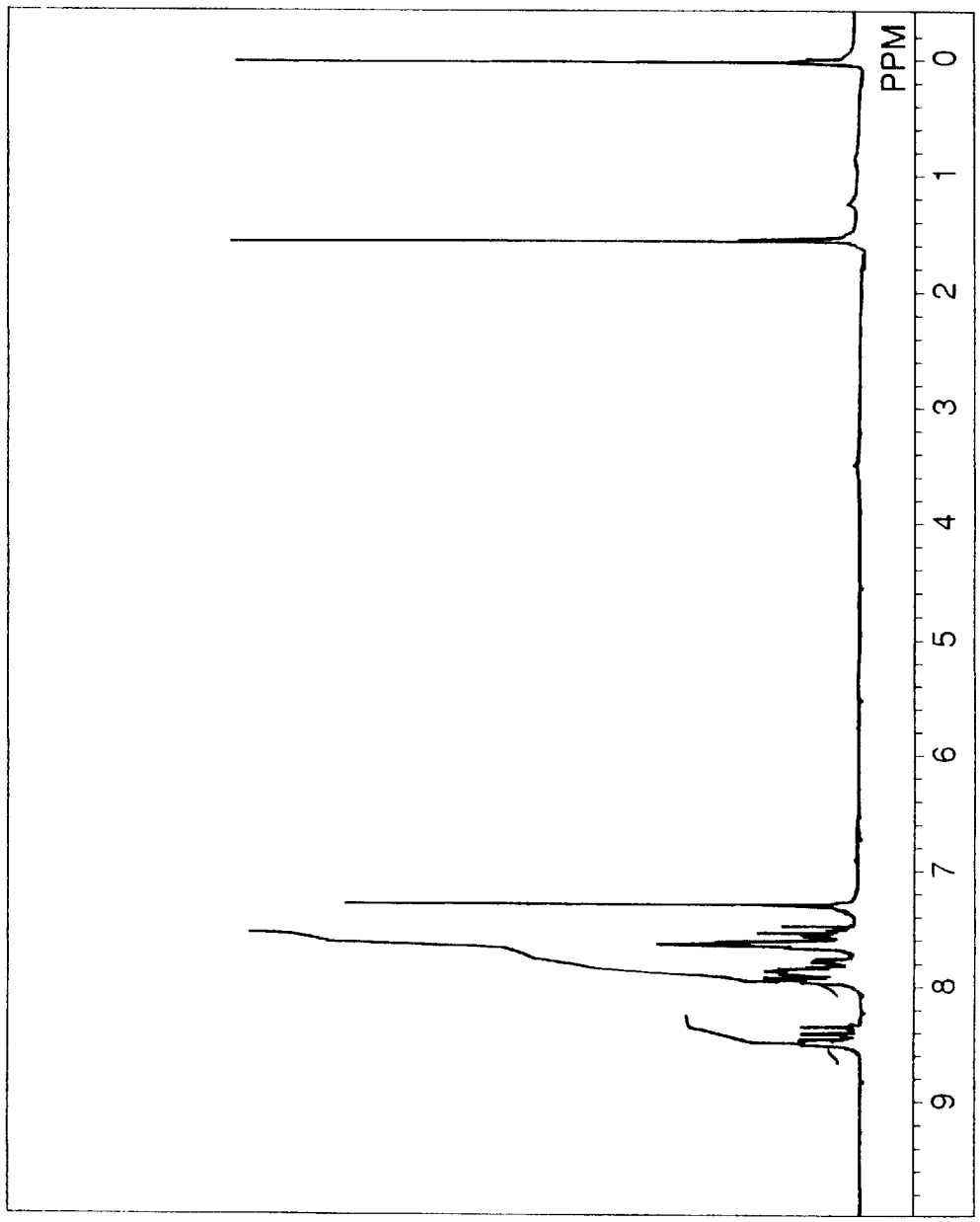
FIG. 8 shows a graph showing the 1H-NMR spectrum of a naphthoquinone derivative (1-4) of this invention.
Figure 9:
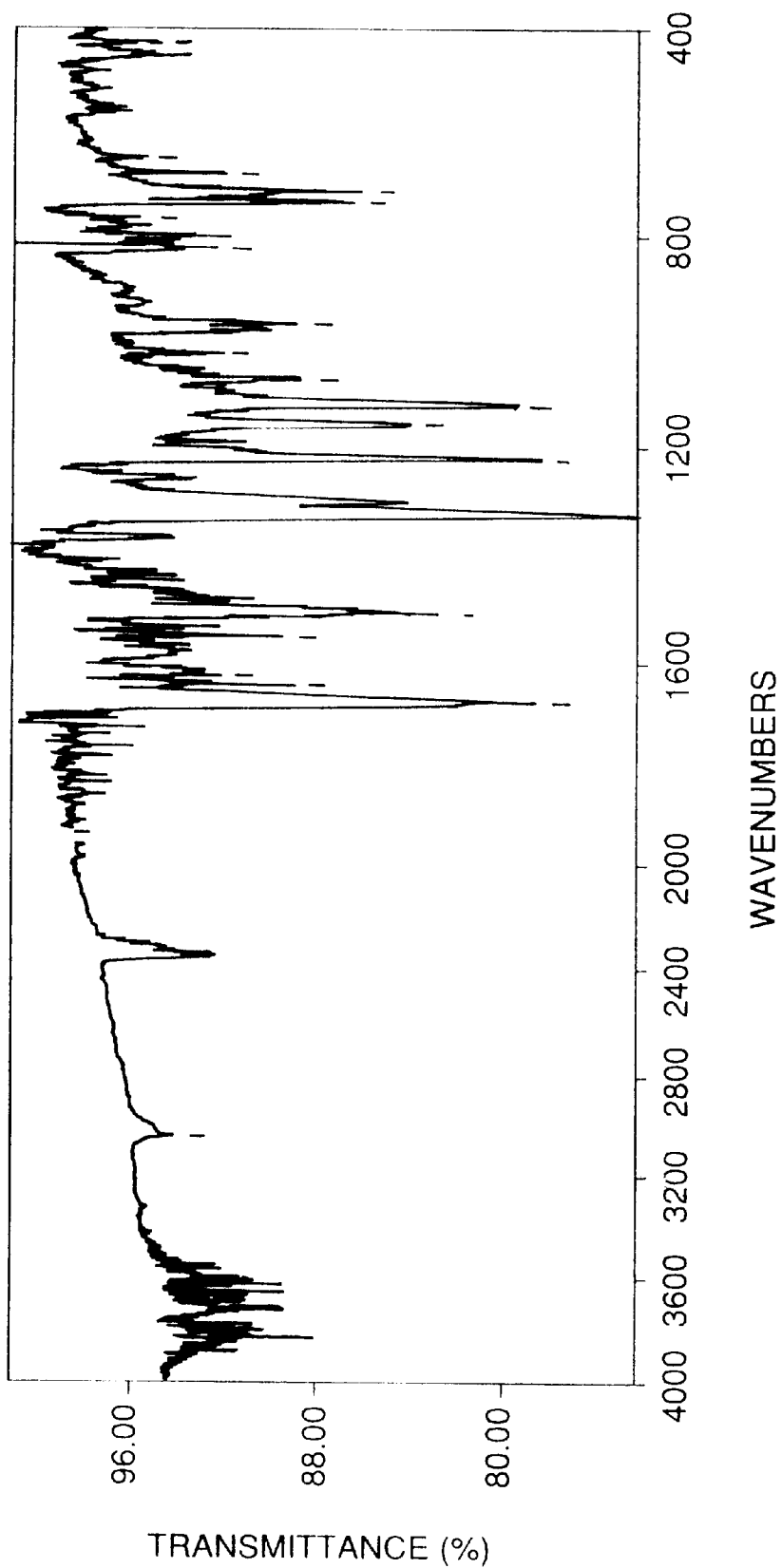
FIG. 9 shows a graph showing the IR spectrum of the naphthoquinone derivative (1-4) of this invention.
Figure 10:
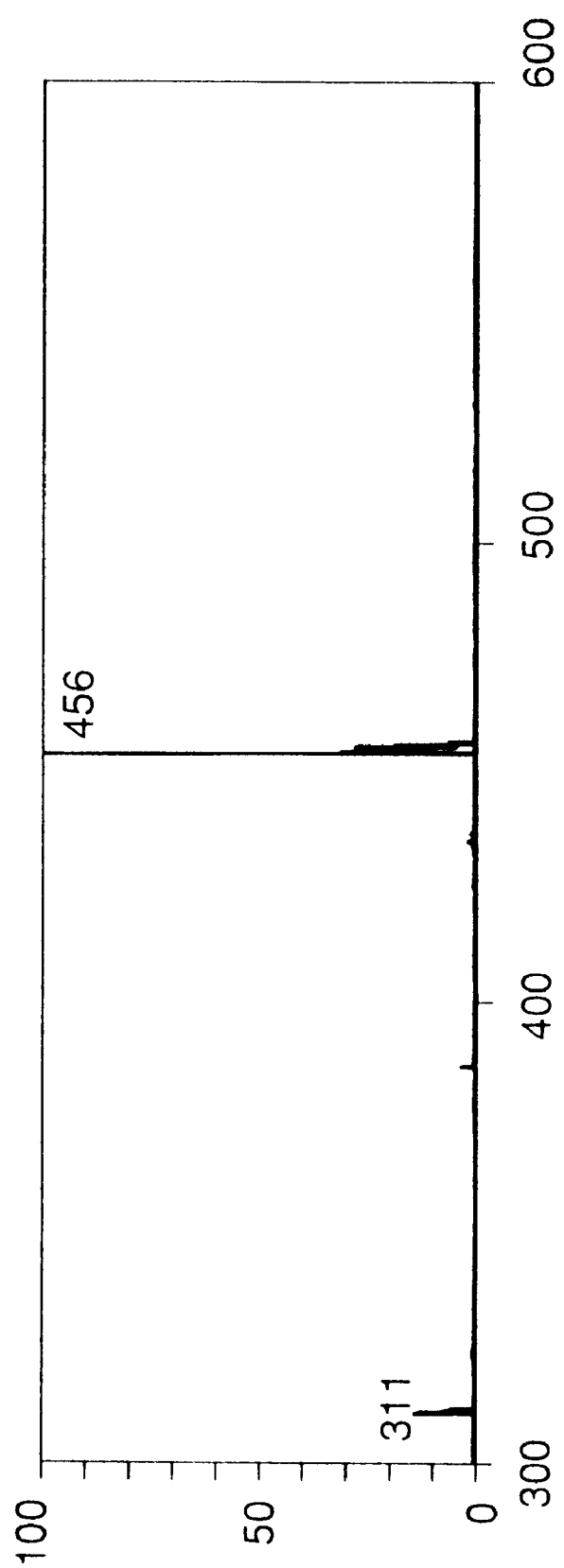
FIG. 10 shows a graph showing the MS spectrum of the naphthoquinone derivative (1-4) of this invention.

The 1H-NMR spectrum of the product is shown in FIG. 8, its IR spectrum is shown in FIG. 9, and its MS spectrum is shown in FIG. 10.

The compound (5-4) is shown below.

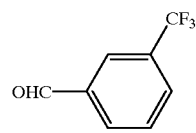

(5-4)

Synthesis Example 5

[Synthesis of a naphthoquinone derivative of the formula (1-5)]

The same Synthesis Example 1 was carried out except that instead of the formula (5-1), (5-5) was used in an amount of 8.6 mmol to give the below-mentioned compound (yielded amount 3.6 g, yield 95.3%). Melting point 271 to 274° C.

Figure 11:
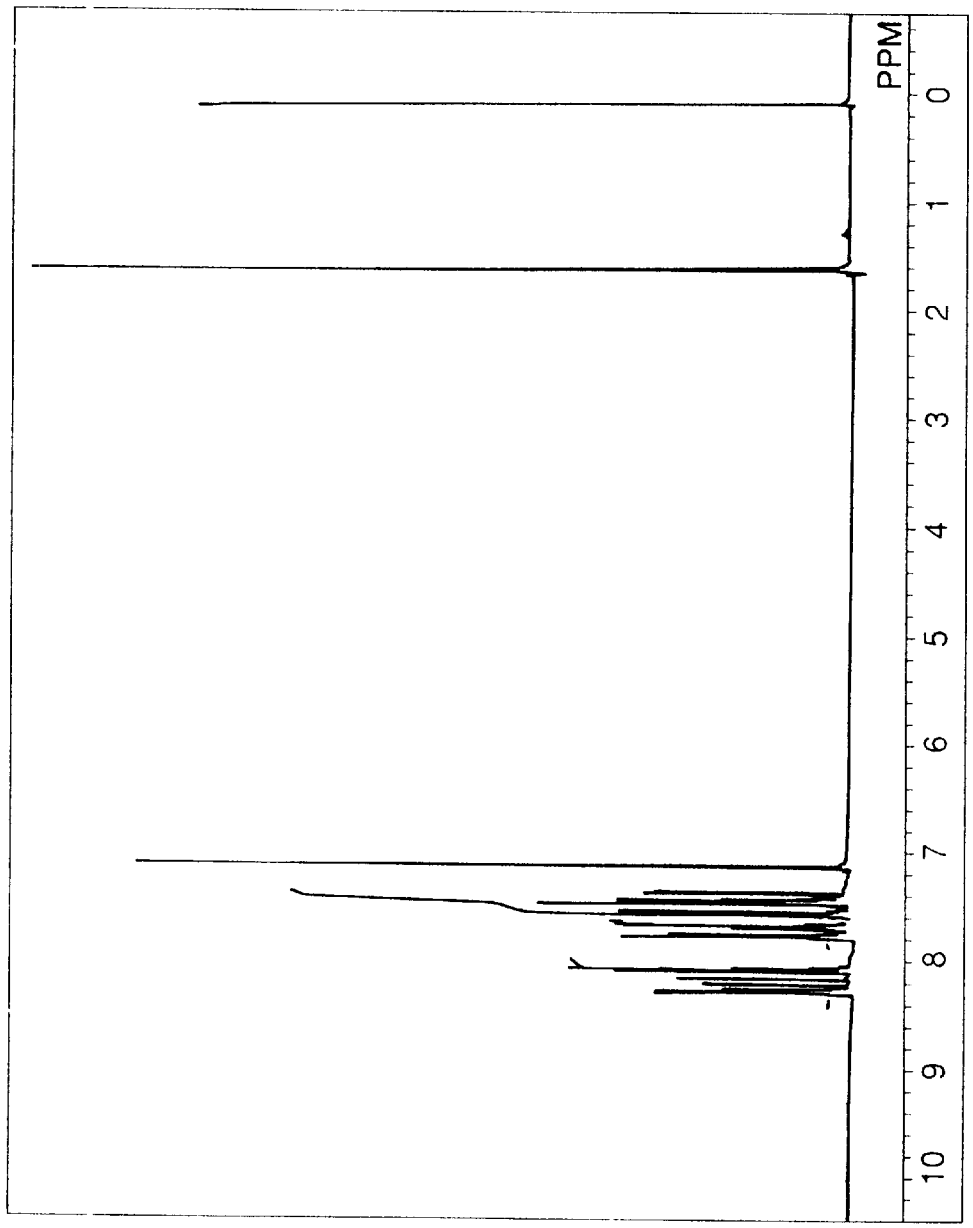
FIG. 11 shows a graph showing the 1H-NMR spectrum of the naphthoquinone derivative (1-4) of this invention.
Figure 12:
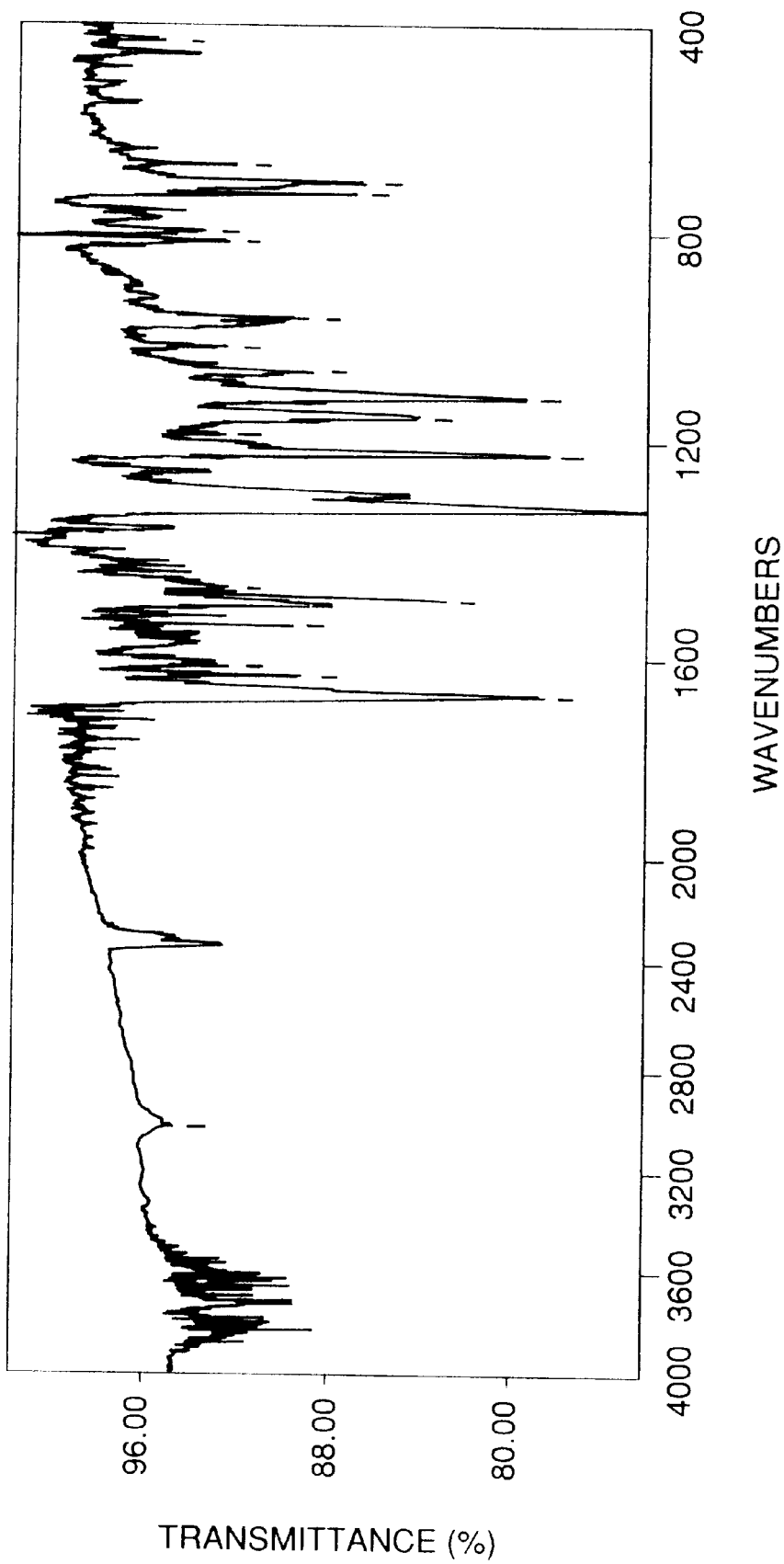
FIG. 12 shows a graph showing the IR spectrum of the naphthoquinone derivative (1-4) of this invention.
Figure 13:
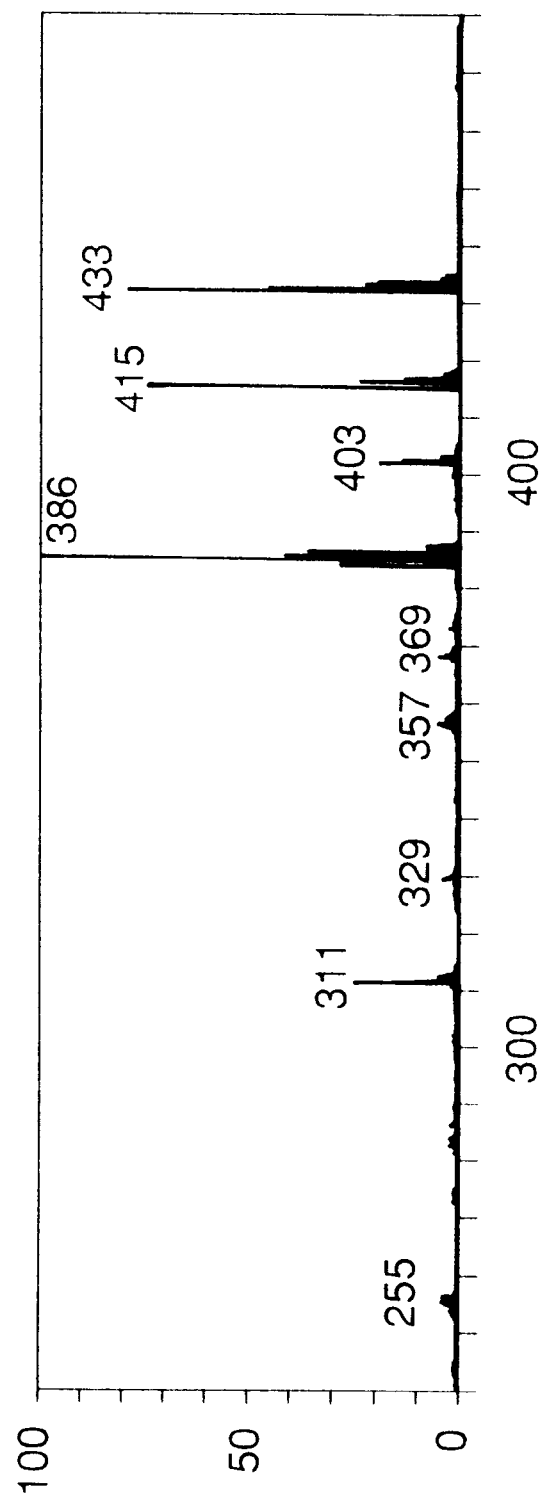
FIG. 13 shows a graph showing the MS spectrum of the naphthoquinone derivative (1-4) of this invention

The 1H-NMR spectrum of the product is shown in FIG. 11, its IR spectrum is shown in FIG. 12, and its MS spectrum is shown in FIG. 13.

The compound (5-5) is shown below.

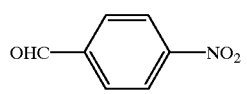

(5-5)

[Production of an electrophotographic photosensitive material]

Components used in the electrophotographic photosensitive materials of this invention are as follows.

(i) Charge generating agents $PcH_2$: X-type non-metallic phthalocyanine expressed by the formula (CG1)[inonization potential (Ip)=5.38 eV]

PcTiO: oxotitanyl phthalocyanine represented by the formula (CG2) [ionization potential (Ip=5.32 eV)]

Perylene: represented by the formula (CG3-1) belonging to the general formula (CG3)

Perylene pigment (Ip=5.50 eV) represented by the following formula (CG3-1) belonging to the general formula (CG3-1)

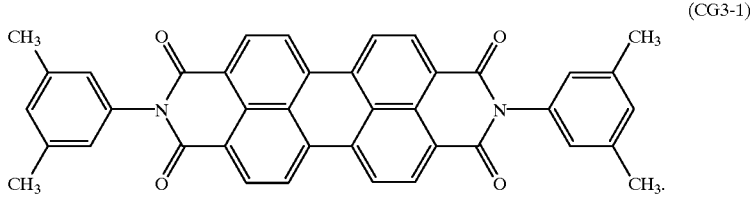

(CG3-1)

(ii) Positive hole transporting agents

HT1-1: a benzidine derivative represented by the formula (HT1-1) (Ip=5.56 eV)

(iii) Electron transporting agents 1-1: a naphthoquinone derivative represented by the formula (1-1)

1-2: a naphthoquinone derivative represented by the formula (1-2)

1-3: a naphthoquinone derivative represented by the formula (1-3)

1-4: a naphthoquinone derivative represented by the formula (1-4)

1-5: a naphthoquinone derivative represented by the formula (1-5)

3-Phenyl-1,4-naphthoquinone expressed by the following formula (ET13-1) which belongs to naphthoquinone derivatives represented by the formula (ET13) disclosed by ET13-1: in Japanese Laid-Open Patent Publication No. 110227/1994

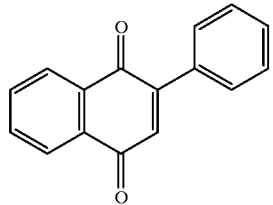

3-1: p-benzoquinone represented by the formula (3-1) (oxidation reduction potential=−0.81 V)

3-2: 2,6-dit-butyl-p-benzoquinone represented by the formula (3-2) (oxidation reduction potential=−1.30 V)

2-1: 3,5-dimethyl-3',5'-dit-butyl-4,4'-diphenoquinone represented by the formula (2-1) (oxidation reduction potential=−0.86 V)

2-2: 3,3',5,5'-tetrat-butyl-4,4'-diphenoquinone represented by the formula (2-2) (oxidation reduction potential=−0.94 V)

The above ionization potentials are measured by a photoelectric analyzing apparatus under atmosphere (AC-1 manufactured by Riken Instrument Co., Ltd.).

[Production of single layer type electrophotographic photosensitive material]

Examples 1 to 15 and Comparative Examples 1 to 8

The charge generating agents, the positive hole transporting agents and the electron transporting agents shown in Tables 1 and 3 together with the binder resins and a solvent were compounded in the proportions given below, and they were mixed and dispersed in a ball mill for 50 hours to prepare a single layer type coating solution for producing a photosensitive material.

| (Components) | (Parts by weight) |
|---|---|
| Charge generating agent | 5 |
| Positive hole transporting agent | 50 |
| Electron transporting agent | 30 |
| Binder resin (polycarbonate) | 100 |
| Solvent (tetrahydrofuran) | 800 |

The coating solution was coated on an aluminum tube as an electroconductive substrate by a dip coating method. The solution was dried by hot air at 100° C. for 60 minutes to prepare a single layer-type electrophotographic photosensitive material having a film thickness of 15 to 20 µm.

Examples 26 to 45 and Comparative Examples 13 to 16

Five parts by weight of the charge generating agent, 50 parts by weight of the positive hole transporting agent and 30 parts by weight of the electron transporting agent shown in Tables 2 and 3, 100 parts by weight of the binder resin and 800 parts by weight of the solvent were mixed, and 10 parts by weight of an electron transporting agent having the formula (2-1) to (2-2) or the formula (3-1) to (3-2) having a predetermined reduction potential was compounded to prepare a single layer-type photosensitive layer coating solution. Otherwise, a single layer-type electrophotographic photosenstive material was prepared in the same way as in Examples 1 to 3.

[Production of a laminated-type electrophotographic photosensitive material]

Examples 16 to 25 and Comparative Examples 9 to 12

One hundred parts by wieght of the charge generating agent described in Tables 1 and 3, 100 parts by weight of a binder resin (polyvinylbutyral), and 2000 weight of a solvent (tetrahydrofuran) were mixed and dispersed in a ball mill for 50 hours to prepare a coating solution for a charge generating layer. This coating solution was applied to the surface of an aluminum tube as an electroconductive substrate by a dip coating method, and dried with hot air at 100° C. for 60 minutes to form a charge generating layer having a film thickness of 1 µm.

Then, 100 parts by weight of the electron transporting agent shown in Tables 1 to 3, 100 parts by weight of the binder resin (polycarbonate) and 800 parts by weight of a solvent (toluene) were mixed and dispersed in a ball mill for 50 hours to prepare a coating solution for a charge transporting layer. This coating solution was coated on the charge generating layer by a dip coating method, and dried with hot air at 100° C. for 60 minutes to form a charge transporing layer having a film thickness of 20 µm and to form a laminated-type electrophotographic photosensitive material.

[Evaluation of the characteristics of the photosensitive material]

The electrophotographic photosensitive materials obtained in the above Examples and Comparative Examples were subjected to the following photosensitive test to evaluated the characteristic of sensitivity. Photosensitivity test By using a drum-type sensitivity tester produced by Gentec Co., Ltd., a voltage was applied to the photosensitive materials of the Examples and Comparative Examples to charge them to +700 V. Then, light was irradiated to the photosensitive materials, and after 330 milliseconds from the exposure, the surface of the photosensitive material was measured as potential VL (V) after the exposure.

Incidentally, the light irradiation conditions were different when the charge generating agent was of a phthalocyanine-type and a perylene-type.

(1) In the case of a phthalocyanine-type pigment:

To the surface of a photosensitive material charged to +700V, a monochromatic light (halogen lamp, light intensity: 16 $\mu W/cm^2$) adjusted to 780 nm (half value width: 20 nm) by using a band pass filter was irradiated for 80 milliseconds.

(2) In the case of a perylene pigment:

To the surface of a photosensitive material charged to +700 V, a white light of a halogen lamp (light intensity: 147 $\mu W/cm^2$) was irradiated for 50 milliseconds.

Components used in the above Examples and Comparative Examples and the results of measuring potentials $V_L$ after the exposure are shown in Tables 1 to 3.

TABLE 1

| Ex. | Charge generating | Positive hole transporting agent | Electron transporting agent | Electron acceptor | $V_L$ (V) |
|---|---|---|---|---|---|
| 1 | PcH$_2$ | HT1-1 | 1-1 | — | — | 181 |
| 2 | PcTiO | HT1-1 | 1-1 | — | — | 182 |
| 3 | Perylene | HT1-1 | 1-1 | — | — | 220 |
| 4 | PcH$_2$ | HT1-1 | 1-2 | — | — | 180 |
| 5 | PcTiO | HT1-1 | 1-2 | — | — | 183 |
| 6 | Perylene | HT1-1 | 1-2 | — | — | 215 |
| 7 | PcH$_2$ | HT1-1 | 1-3 | — | — | 178 |
| 8 | PcTiO | HT1-1 | 1-3 | — | — | 180 |
| 9 | Perylene | HT1-1 | 1-3 | — | — | 220 |
| 10 | PcH$_2$ | HT1-1 | 1-4 | — | — | 179 |
| 11 | PcTiO | HT1-1 | 1-4 | — | — | 180 |
| 12 | Perylene | HT1-1 | 1-4 | — | — | 221 |
| 13 | PcH$_2$ | HT1-1 | 1-5 | — | — | 178 |
| 14 | PcTiO | HT1-1 | 1-5 | — | — | 175 |
| 15 | Perylene | HT1-1 | 1-5 | — | — | 213 |
| 16 | PcH$_2$ | — | 1-1 | — | — | 263 |
| 17 | Perylene | — | 1-1 | — | — | 281 |
| 18 | PcH$_2$ | — | 1-2 | — | — | 260 |
| 19 | Perylene | — | 1-2 | — | — | 283 |
| 20 | PcH$_2$ | — | 1-3 | — | — | 263 |
| 21 | Perylene | — | 1-3 | — | — | 285 |
| 22 | PcH$_2$ | — | 1-4 | — | — | 263 |
| 23 | Perylene | — | 1-4 | — | — | 283 |
| 24 | PcH$_2$ | — | 1-5 | — | — | 263 |
| 25 | Perylene | — | 1-5 | — | — | 285 |

TABLE 2

| Ex. | Charge generating agent | Positive hole transporting agent | Electron transporting agent | | $V_L$ (V) |
|---|---|---|---|---|---|
| 26 | PCH$_2$ | HT1-1 | 1-1 | 3-1 | 135 |
| 27 | PCH$_2$ | HT1-1 | 1-1 | 3-2 | 130 |
| 28 | PCH$_2$ | HT1-1 | 1-1 | 2-1 | 125 |
| 29 | PCH$_2$ | HT1-1 | 1-1 | 2-2 | 123 |
| 30 | PCH$_2$ | HT1-1 | 1-2 | 3-1 | 139 |
| 31 | PCH$_2$ | HT1-1 | 1-2 | 3-2 | 134 |
| 32 | PCH$_2$ | HT1-1 | 1-2 | 2-1 | 127 |
| 33 | PCH$_2$ | HT1-1 | 1-2 | 2-2 | 125 |
| 34 | PCH$_2$ | HT1-1 | 1-3 | 3-1 | 139 |
| 35 | PCH$_2$ | HT1-1 | 1-3 | 3-2 | 135 |
| 36 | PCH$_2$ | HT1-1 | 1-3 | 2-1 | 127 |
| 37 | PCH$_2$ | HT1-1 | 1-3 | 2-2 | 123 |
| 38 | PCH$_2$ | HT1-1 | 1-4 | 3-1 | 138 |
| 39 | PCH$_2$ | HT1-1 | 1-4 | 3-2 | 134 |
| 40 | PCH$_2$ | HT1-1 | 1-4 | 2-1 | 126 |
| 41 | PCH$_2$ | HT1-1 | 1-4 | 2-2 | 122 |
| 42 | PCH$_2$ | HT1-1 | 1-5 | 3-1 | 136 |
| 43 | PCH$_2$ | HT1-1 | 1-5 | 3-2 | 132 |
| 44 | PCH$_2$ | HT1-1 | 1-5 | 2-1 | 124 |
| 45 | PCH$_2$ | HT1-1 | 1-5 | 2-2 | 120 |

TABLE 3

| Comp. Ex. | Charge generating agent | Positive hole transporting agent | Electron transporting agent | | $V_L$ (V) |
|---|---|---|---|---|---|
| 1 | PcH$_2$ | HT1-1 | ET13-1 | — | 305 |
| 2 | PcTiO | HT1-1 | ET13-1 | — | 330 |
| 3 | Perylene | HT1-1 | ET13-1 | — | 375 |
| 4 | PcH$_2$ | HT1-1 | 2-1 | — | 220 |
| 5 | PcTiO | HT1-1 | 2-1 | — | 242 |
| 6 | PcH$_2$ | HT1-1 | — | — | 478 |
| 7 | Perylene | HT1-1 | 2-1 | — | 294 |
| 8 | Perylene | HT1-1 | — | — | 521 |
| 9 | PcH$_2$ | — | ET13-1 | — | 409 |
| 10 | perylene | — | ET13-1 | — | 455 |
| 11 | PcH$_2$ | — | 2-1 | — | 346 |
| 12 | perylene | — | 2-1 | — | 386 |
| 13 | PcH$_2$ | HT1-1 | ET13-1 | 3-1 | 295 |
| 14 | PcH$_2$ | HT1-1 | ET13-1 | 3-2 | 290 |
| 15 | Perylene | HT1-1 | ET13-1 | 2-1 | 290 |
| 16 | Perylene | HT1-1 | ET13-1 | 2-2 | 288 |

As is clear from Tables 1 to 3, the photosensitive materials of Examples had lower potentials after the exposure than the conventional photosensitive materials containing the conventional electron transporting agents or the photosensitive materials of Comparative Examples not containing the electron transporting agent and had higher sensitivity.

Furthermore, since the photosensitive materials of Examples 21 to 36 had the electron transporting agents having predetermined oxidation reduction potentials and the naphthoquinone derivatives (1) of the present invention, they had lower potentials after the exposure than the photosensitive materials the other Examples, and therefore had higher sensitivity.

The naphthoquinone derivatives (1) used in the electrophotographic phosensitive materials of this invention have high electron transporting ability. Accordingly, the electrophotographic photosensitive materials containing the naphthoquinone derivatives (1) as electron transporting agents have markedly lowered residual potentials, and have high sensitivity.

By further adding an electron transporting agent having a predetermined oxidation reduction potential, the residual potential is further lowered, and photosensitive materials having increased sensitivity can be obtained.

The use of the photosensitive materials of this invention makes it possibe to increase the speeds of copying machines and printers.

What is claimed is:

1. An electrophotographic photosensitive material obtained by forming a photosensitive layer containing a naphthoquinone derivative represented by the general formula (1)

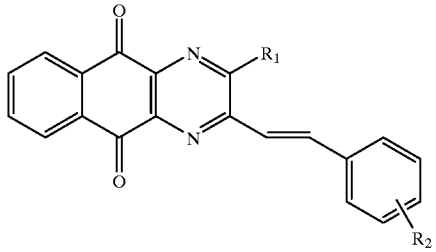
(1)

wherein $R_1$ represents a hydrogen atom, an alkyl group which may have a substituent, an aryl group which may have a substituent, and $R_2$ represents a hydrogen atom, an alkyl group which may have a substituent, a halogenated alkyl group, an aldehyde group, a nitro group or a group (i)

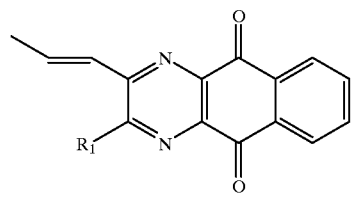
(i)

on an electroconductive substrate.

2. An electrophotographic photosensitive material according to claim 1 wherein the photosensitive layer contains an electron transporting agent having an oxidation reduction potential of −0.8 to −1.4 V.

3. An electrophotographic photosensitive material according to claim 2 wherein the electron transporting agent is a diphenoquinone derivative having a general formula (2)

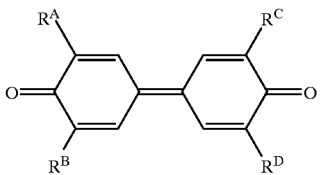
(2)

wherein $R^A$, $R^B$, $R^C$ and $R^D$ may be the same or different, and each represents a hydrogen atom, an alkyl group, an alkoxy group, an aryl group, an aralkyl group, a cycloalkyl group or an amino group, or a benzoquinone derivative having a general formula (3)

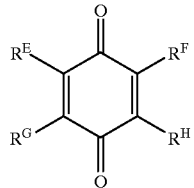
(3)

wherein $R^E$, $R^F$, $R^G$ and $R^H$ may be the same or different and each represents a hydrogen atom, an alkyl group, an alkoxy group, an aryl group, an aralkyl group, a cycloalkyl group or an amino group which may have a substituent.

* * * * *